US010893988B2

(12) United States Patent
Tessmer et al.

(10) Patent No.: US 10,893,988 B2
(45) Date of Patent: Jan. 19, 2021

(54) PATIENT SUPPORT SYSTEMS AND METHODS FOR DOCKING, TRANSPORTING, STERILIZING, AND STORING PATIENT SUPPORT DECKS

(71) Applicant: Stryker Corporation, Kalamazoo, MI (US)

(72) Inventors: Brian Tessmer, Kalamazoo, MI (US); Lance Erick Larsen, Grand Rapids, MI (US); Cecil Alan Myers, Vicksburg, MI (US)

(73) Assignee: Stryker Corporation, Kalamazoo, MI (US)

( * ) Notice: Subject to any disclaimer, the term of this patent is extended or adjusted under 35 U.S.C. 154(b) by 577 days.

(21) Appl. No.: 15/602,384

(22) Filed: May 23, 2017

(65) Prior Publication Data

US 2017/0340498 A1    Nov. 30, 2017

Related U.S. Application Data

(60) Provisional application No. 62/341,859, filed on May 26, 2016.

(51) Int. Cl.
*A61G 1/00*    (2006.01)
*A61G 13/10*    (2006.01)
(Continued)

(52) U.S. Cl.
CPC .............. *A61G 1/00* (2013.01); *A61B 6/0407* (2013.01); *A61G 1/0293* (2013.01); *A61G 1/04* (2013.01);
(Continued)

(58) Field of Classification Search
CPC .......... A61G 1/00; A61G 1/04; A61G 1/0293; A61G 13/105; A61G 13/0018; A61G 13/104; A61B 6/0407
See application file for complete search history.

(56) References Cited

U.S. PATENT DOCUMENTS 4,894,876 A * 1/1990 Fenwick ............ A61G 13/0009
5/602
4,945,592 A    8/1990 Sims et al.
(Continued)

FOREIGN PATENT DOCUMENTS

AU    2012211373 A1    3/2013
CN    201558247 U    8/2010
(Continued)

OTHER PUBLICATIONS

TUG: Smart Autonomous Mobile Robot Brochure, Aethon; 6 pages. URL: http://www.aethon.com/.
(Continued)

*Primary Examiner* — David R Hare
*Assistant Examiner* — Alexis Felix Lopez
(74) *Attorney, Agent, or Firm* — Howard & Howard Attorneys PLLC

(57) ABSTRACT

Patient support systems and methods for docking, transporting, sterilizing, and storing patient support decks. The patient support system comprises patient support decks that are configured to carry patients, such as in emergency situations or in a healthcare facility. The patient support decks are adapted to be engaged by docking stations and transport devices. Different configurations of docking stations and transport devices are contemplated. Sterilization apparatuses are provided to sterilize the patient support decks after use and storage facilities store the patient support decks for later use once they are sterilized.

26 Claims, 18 Drawing Sheets

(51) Int. Cl.

| | |
|---|---|
| A61G 13/00 | (2006.01) |
| A61B 6/04 | (2006.01) |
| A61G 1/02 | (2006.01) |
| A61G 1/04 | (2006.01) |
| A61L 2/26 | (2006.01) |
| G16H 40/63 | (2018.01) |
| A61L 2/20 | (2006.01) |
| A61L 2/08 | (2006.01) |
| A61L 2/07 | (2006.01) |

(52) U.S. Cl.
CPC ....... *A61G 13/0018* (2013.01); *A61G 13/104* (2013.01); *A61G 13/105* (2013.01); *A61L 2/26* (2013.01); *G16H 40/63* (2018.01); *A61G 13/107* (2013.01); *A61G 2203/22* (2013.01); *A61G 2203/44* (2013.01); *A61G 2205/60* (2013.01); *A61G 2210/50* (2013.01); *A61L 2/07* (2013.01); *A61L 2/081* (2013.01); *A61L 2/206* (2013.01); *A61L 2/208* (2013.01)

(56) References Cited

U.S. PATENT DOCUMENTS

| | | | |
|---|---|---|---|
| 4,985,947 A | | 1/1991 | Ethridge |
| 5,023,968 A | * | 6/1991 | Diehl .................. A61G 1/017 403/102 |
| 5,083,331 A | * | 1/1992 | Schnelle ............. A61G 7/1019 403/327 |
| 5,319,816 A | | 6/1994 | Ruehl |
| 5,411,044 A | | 5/1995 | Andolfi |
| 5,475,884 A | | 12/1995 | Kirmse et al. |
| 5,513,406 A | | 5/1996 | Foster et al. |
| 5,535,141 A | | 7/1996 | Lussi |
| 6,101,644 A | | 8/2000 | Gagneur et al. |
| 6,183,417 B1 | | 2/2001 | Geheb et al. |
| 6,378,883 B1 | | 4/2002 | Epstein |
| 6,585,206 B2 | | 7/2003 | Metz et al. |
| 6,725,474 B2 | | 4/2004 | Foster et al. |
| 6,895,715 B2 | * | 5/2005 | Gallant ................. A61G 7/00 52/29 |
| 6,978,499 B2 | * | 12/2005 | Gallant ................. A61G 1/00 5/507.1 |
| 7,137,160 B2 | | 11/2006 | Hand et al. |
| 7,243,386 B2 | | 7/2007 | Gallant et al. |
| 7,314,200 B2 | | 1/2008 | Bally et al. |
| 7,418,749 B2 | | 9/2008 | Graham et al. |
| 7,481,286 B2 | | 1/2009 | Ruschke et al. |
| 7,497,407 B2 | | 3/2009 | Blankenship et al. |
| 7,570,152 B2 | | 8/2009 | Smith et al. |
| 7,636,966 B2 | | 12/2009 | Gallant et al. |
| 7,735,788 B2 | | 6/2010 | Newkirk et al. |
| 7,735,789 B2 | | 6/2010 | Blankenship et al. |
| 7,742,562 B2 | * | 6/2010 | Weber ................. A61B 6/0457 378/209 |
| 7,845,601 B1 | | 12/2010 | Culpepper et al. |
| 7,865,983 B2 | | 1/2011 | Newkirk et al. |
| 7,938,756 B2 | | 5/2011 | Rodetsky et al. |
| 7,971,893 B2 | | 7/2011 | Dunn |
| 8,005,686 B2 | | 8/2011 | Smith |
| 8,056,162 B2 | | 11/2011 | Newkirk et al. |
| 8,100,371 B2 | | 1/2012 | Eggleston et al. |
| 8,104,729 B2 | | 1/2012 | Walke et al. |
| 8,132,276 B2 | | 3/2012 | Klemm et al. |
| 8,334,779 B2 | | 12/2012 | Zerhusen et al. |
| 8,336,134 B2 | | 12/2012 | Jelinek |
| 8,468,625 B2 | | 6/2013 | Schreuder et al. |
| 8,516,637 B2 | | 8/2013 | Karwal et al. |
| 8,535,214 B2 | | 9/2013 | Chilton, III |
| 8,544,866 B2 | | 10/2013 | Noonan et al. |
| 8,756,078 B2 | | 6/2014 | Collins, Jr. et al. |
| RE45,058 E | | 8/2014 | Blankenship et al. |
| 8,826,475 B2 | | 9/2014 | Jackson |
| 8,864,205 B2 | | 10/2014 | Lemire et al. |
| 9,138,173 B2 | | 9/2015 | Penninger et al. |
| 9,192,534 B2 | | 11/2015 | Coppens et al. |
| 9,220,651 B2 | | 12/2015 | Hyde et al. |
| 9,223,313 B2 | | 12/2015 | Wolfe et al. |
| 9,289,336 B2 | | 3/2016 | Lambarth et al. |
| 9,480,615 B2 | * | 11/2016 | Eisenmann .......... A61G 13/104 |
| 9,486,373 B2 | | 11/2016 | Lambarth et al. |
| 9,510,981 B2 | | 12/2016 | Lambarth et al. |
| 9,528,536 B2 | | 12/2016 | Bally et al. |
| 9,569,591 B2 | | 2/2017 | Vanderpohl, III |
| 2002/0116760 A1 | | 8/2002 | Foster et al. |
| 2003/0009825 A1 | | 1/2003 | Gallant et al. |
| 2004/0111800 A1 | | 6/2004 | Bartels et al. |
| 2004/0201191 A1 | | 10/2004 | Jacques et al. |
| 2005/0017468 A1 | | 1/2005 | Gallant et al. |
| 2006/0179571 A1 | | 8/2006 | Newkirk |
| 2006/0249635 A1 | | 11/2006 | Newkirk et al. |
| 2008/0005840 A1 | * | 1/2008 | Zelnik .................. A47C 20/00 5/601 |
| 2008/0312971 A2 | | 12/2008 | Rosow et al. |
| 2009/0281658 A1 | | 11/2009 | Huttenberger et al. |
| 2011/0154569 A1 | * | 6/2011 | Wiggers ............... A61B 6/0407 5/81.1 R |
| 2011/0208541 A1 | | 8/2011 | Wilson et al. |
| 2012/0075464 A1 | | 3/2012 | Derenne et al. |
| 2012/0139197 A1 | * | 6/2012 | Livingston ............ A61G 5/061 280/5.22 |
| 2012/0283746 A1 | | 11/2012 | Hu et al. |
| 2012/0330087 A1 | | 12/2012 | Gregerson |
| 2013/0205501 A1 | | 8/2013 | Robertson et al. |
| 2014/0033432 A1 | * | 2/2014 | Marle .................. A61G 7/1057 5/601 |
| 2014/0034061 A1 | | 2/2014 | Marle et al. |
| 2014/0080413 A1 | | 3/2014 | Hayes et al. |
| 2014/0150806 A1 | | 6/2014 | Hu et al. |
| 2014/0297327 A1 | | 10/2014 | Heil et al. |
| 2014/0310876 A1 | * | 10/2014 | Roussy ................. A61G 7/015 5/613 |
| 2014/0343968 A1 | | 11/2014 | Wilson et al. |
| 2015/0216606 A1 | | 8/2015 | Bally et al. |
| 2015/0359915 A1 | | 12/2015 | Farren et al. |
| 2015/0367008 A1 | | 12/2015 | Romo et al. |
| 2016/0000995 A1 | | 1/2016 | Blankenship et al. |
| 2016/0022900 A1 | | 1/2016 | Pryor et al. |
| 2016/0077524 A1 | | 3/2016 | Hyde et al. |
| 2016/0120723 A1 | * | 5/2016 | Giulianotti .......... A61G 10/005 600/21 |
| 2016/0148485 A1 | | 5/2016 | Hayes et al. |
| 2016/0157951 A1 | | 6/2016 | Schoenig et al. |
| 2016/0158083 A1 | * | 6/2016 | Lambarth ............. A61G 1/0268 5/600 |
| 2016/0166216 A1 | * | 6/2016 | Igney .................. A61B 6/0407 356/614 |
| 2016/0367415 A1 | | 12/2016 | Hayes et al. |
| 2017/0035628 A1 | * | 2/2017 | Naber .................... A61G 1/04 |
| 2017/0130447 A1 | * | 5/2017 | Lane, Jr. ............ E04B 1/34336 |

FOREIGN PATENT DOCUMENTS

| | | |
|---|---|---|
| CN | 101480370 B | 1/2011 |
| CN | 103027827 A | 4/2013 |
| CN | 104757989 A | 7/2015 |
| DE | 102004013585 A1 | 10/2005 |
| EP | 629410 A1 | 12/1994 |
| EP | 1032350 B1 | 2/2002 |
| EP | 1690517 A2 | 8/2006 |
| EP | 1434546 B1 | 5/2010 |
| EP | 2110162 B1 | 5/2011 |
| EP | 2174670 B1 | 4/2013 |
| EP | 2482860 B1 | 8/2014 |
| FR | 2796548 A1 | 1/2001 |
| GB | 2518072 B | 8/2015 |
| KR | 20130076922 A | 7/2013 |
| WO | 2002039944 A3 | 9/2002 |
| WO | 2004039300 A1 | 5/2004 |
| WO | 2005051278 A1 | 6/2005 |

(56) References Cited

FOREIGN PATENT DOCUMENTS

| WO | 2011055173 A1 | 5/2011 |
|---|---|---|
| WO | 2012168760 A1 | 12/2012 |
| WO | 2014029998 A1 | 2/2014 |

OTHER PUBLICATIONS

Hill-Rom, "Latitude (R) Arm System, Taking patient care in a new direction", Mar. 2014; 4 pages.

English language abstract and computer-generated translation for CN103027827 extracted from espacenet.com on Jan. 17, 2018; 4 pages.

English language abstract and computer-generated translation for CN104757989 extracted from espacenet.com database on Jan. 17, 2018; 11 pages.

English language abstract and computer-generated translation for CN201558247 extracted from espacenet.com on Jan. 16, 2018; 9 pages.

English language abstract and computer-generated translation for CN101480370 extracted from espacenet.com on Jan. 17, 2018; 6 pages.

English language abstract and computer-generated translation for FR2796548 extracted from espacenet.com on Jan. 17, 2015; 4 pages.

English language abstract and computer-generated translation for WO2005051278 extracted from espacenet.com on Jan. 17, 2018; 4 pages.

Hill-Rom, "Room of the Future"; available at least as early as May 26, 2016; URL: http://web.archive.org/web/20151007020747/http://www.hill-rom.com:80/usa/Services/Category/Design-Services/Room-of-the-Future/.

Stryker Medical, "InTouch Critical Care Bed Brochure", Aug. 2014, Rev. D, 125 pages.

English language abstract and machine-assisted English translation for DE 10 2004 013 585 extracted from espacenet.com database on May 2, 2018, 25 pages.

English language abstract and machine-assisted English translation for KR 2013-0076922 extracted from espacenet.com database on May 2, 2018, 8 pages.

\* cited by examiner

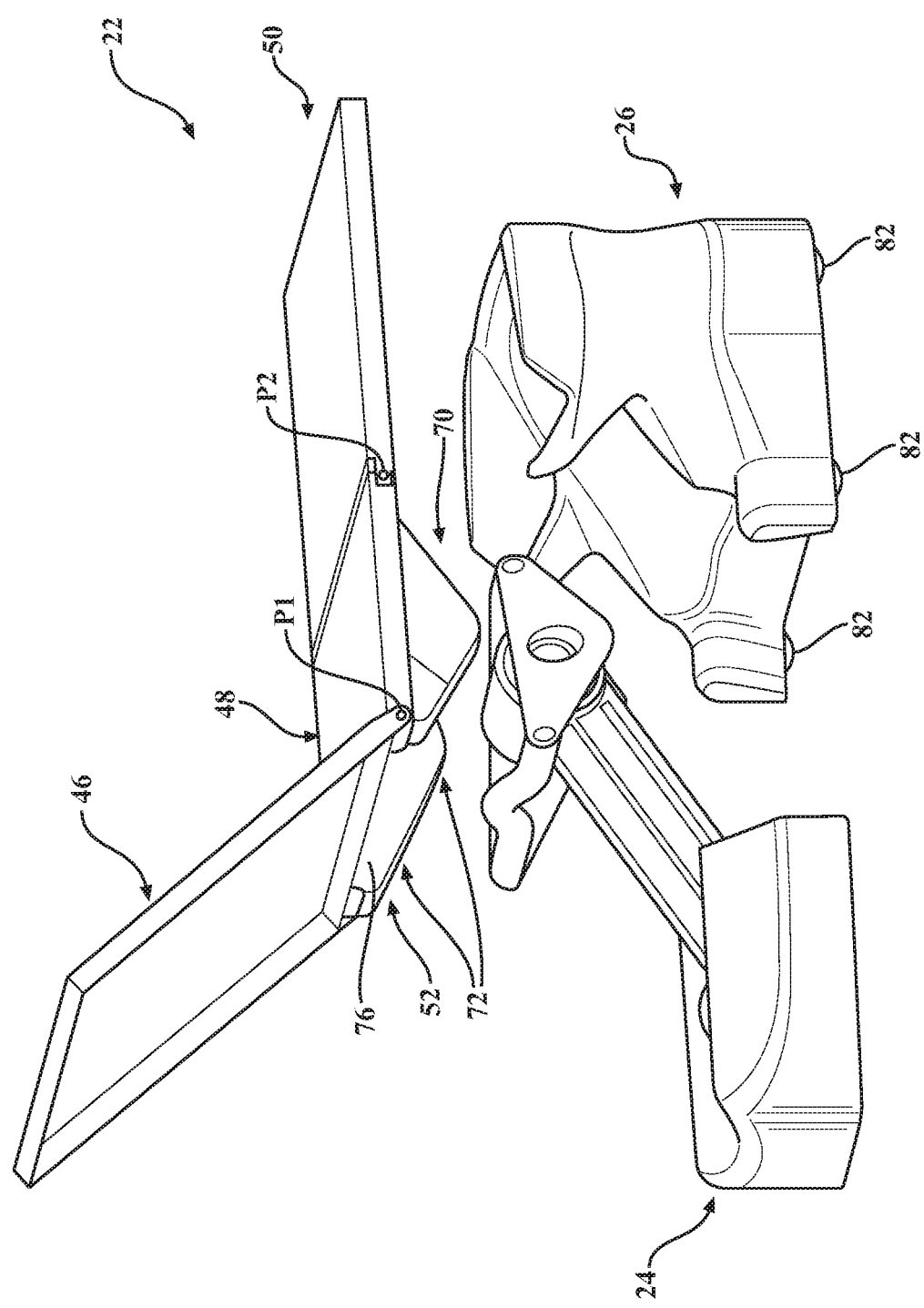

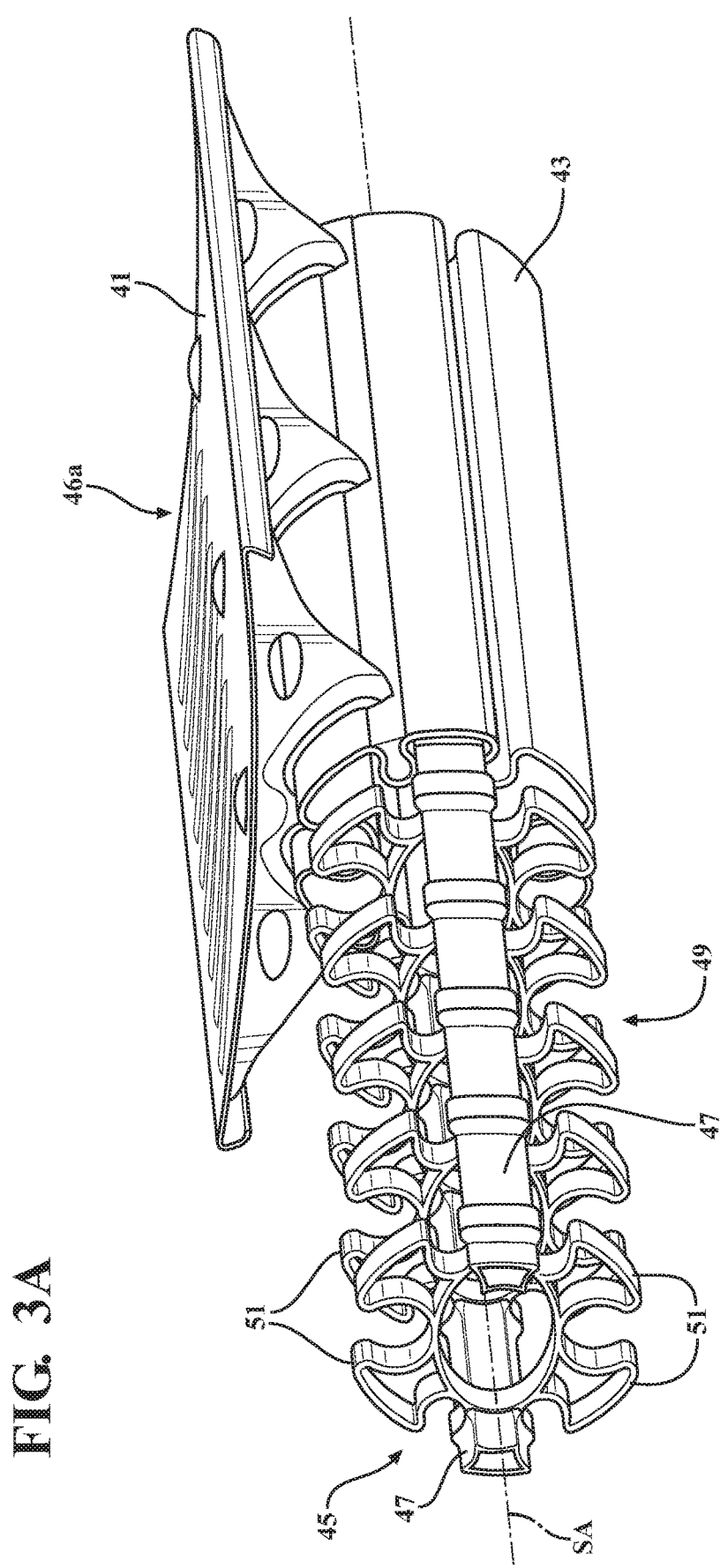

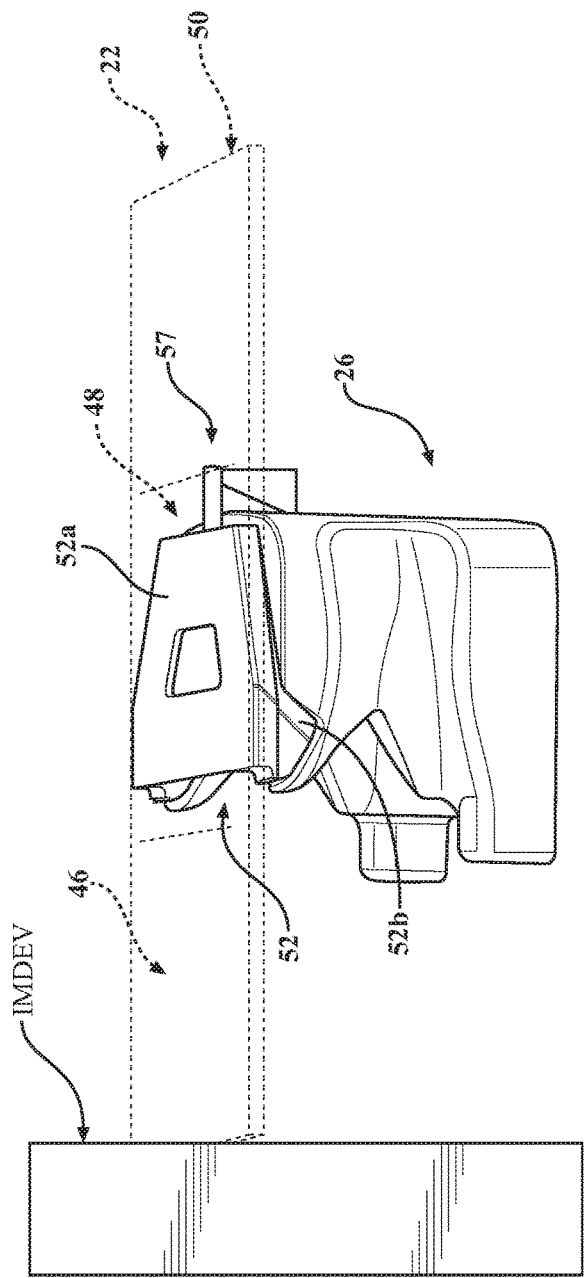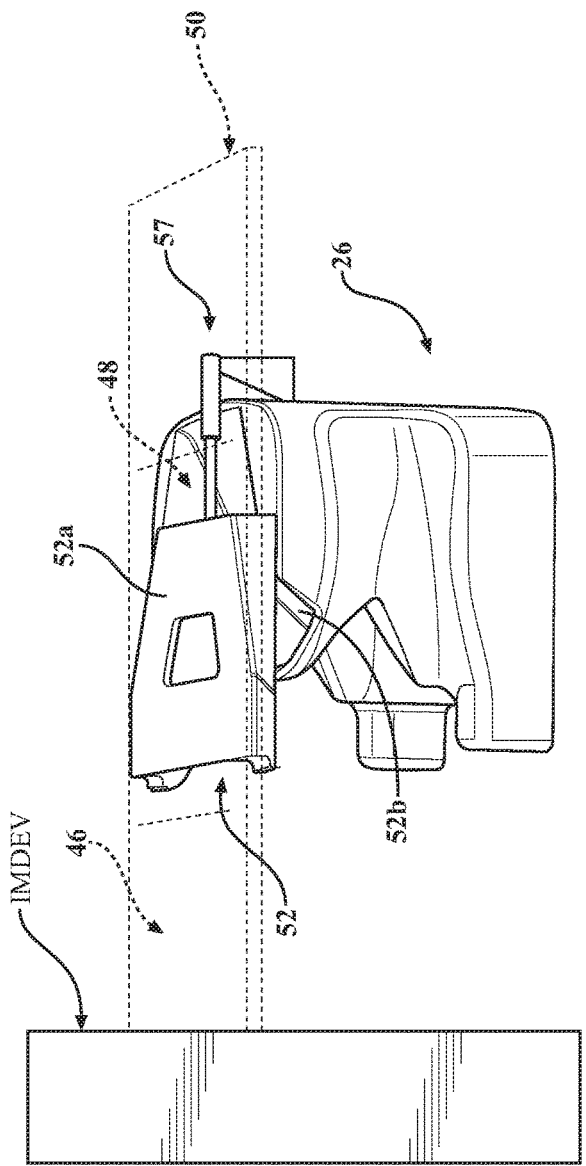
FIG. 5A
FIG. 5B

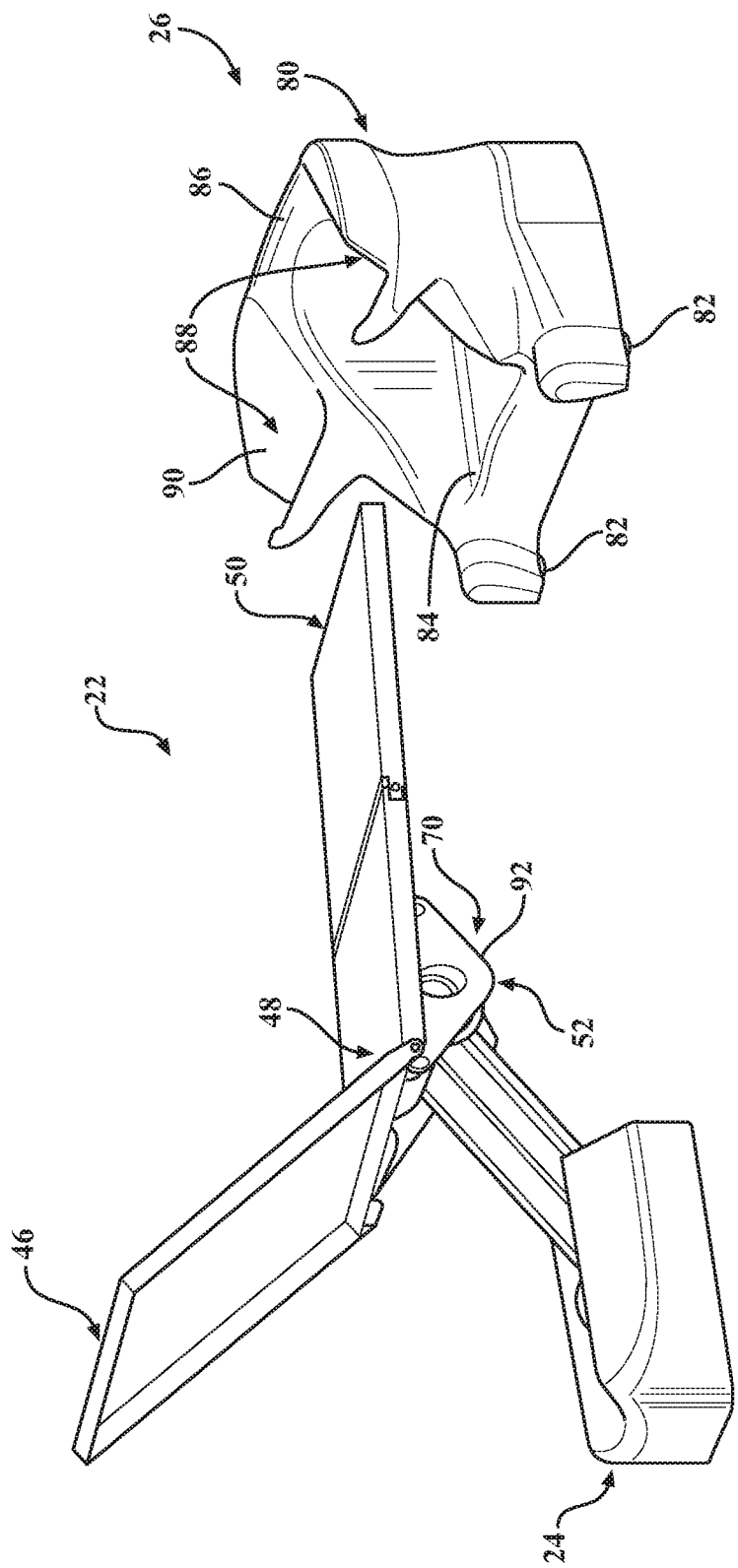

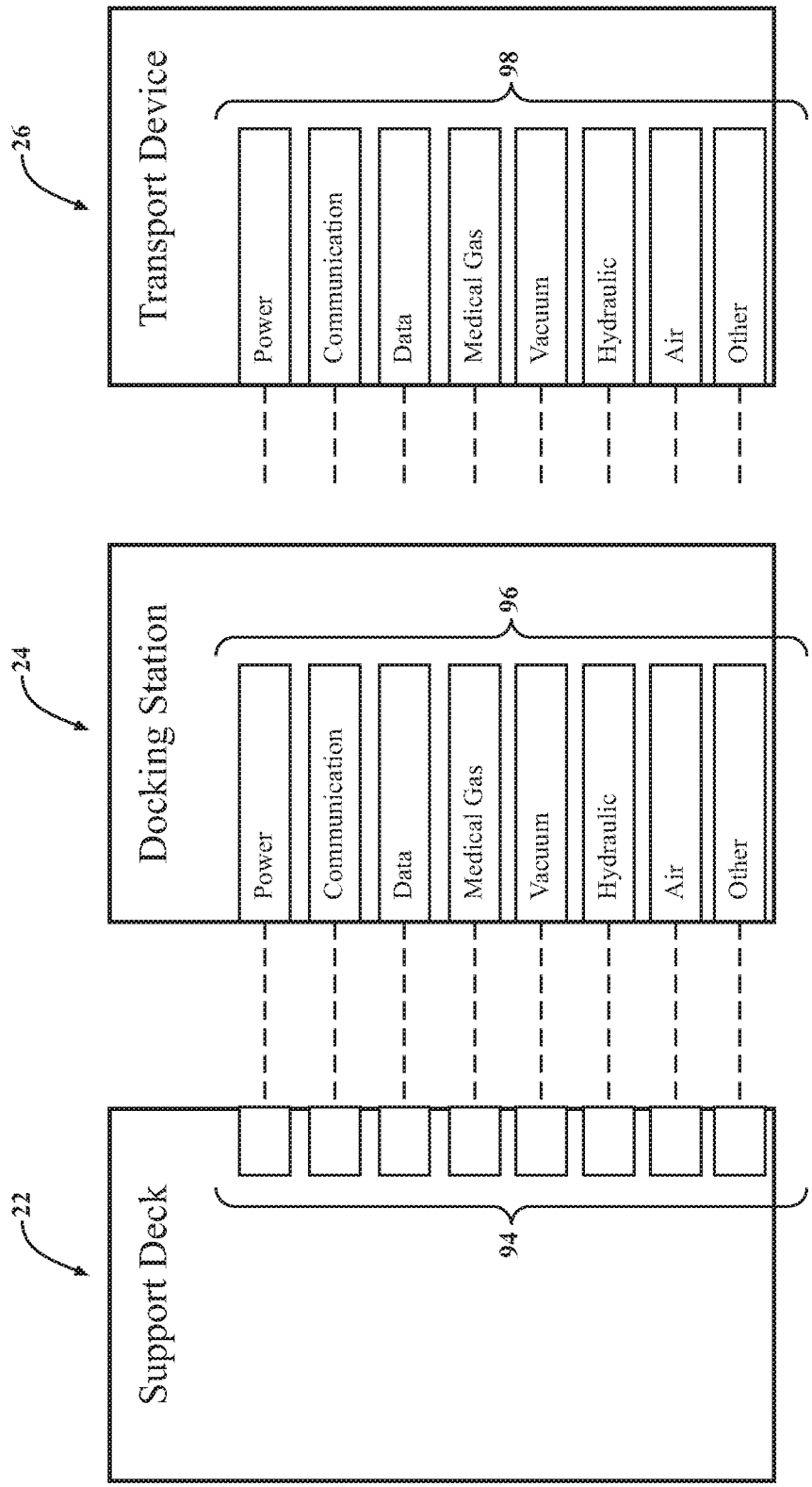

US 10,893,988 B2

PATIENT SUPPORT SYSTEMS AND METHODS FOR DOCKING, TRANSPORTING, STERILIZING, AND STORING PATIENT SUPPORT DECKS

RELATED APPLICATION

This application claims priority to and the benefit of U.S. Provisional Patent Application No. 62/341,859, filed on May 26, 2016, the entire content of which is hereby incorporated by reference herein.

BACKGROUND

Patient support systems typically employ patient support apparatuses, such as hospital beds, stretchers, and wheelchairs, to facilitate care of patients in a health care setting. Conventional patient support apparatuses comprise a base, a support frame, and a patient support deck upon which the patient is supported. Further, conventional patient support apparatuses provide several actuators for lifting/lowering the support frame relative to the base and/or for raising/lowering one or more deck sections of the patient support deck. They also comprise features that make the patient support apparatus mobile, such as wheels on the base, while at the same time providing suitable on-board power for operating the actuators or other powered features during transport. The result of all of these features is that conventional patient support apparatuses can be bulky and expensive. As a result, they can be difficult or cumbersome to transport, sterilize, and/or store.

Additionally, during the course of treating a typical patient, the patient is required to be transferred between several different patient support apparatuses, further escalating costs and inconvenience. For example, a single patient may be initially supported on a stretcher and wheeled into a healthcare facility. The patient then may be transferred to a hospital bed. Later, the same patient may be transferred to an imaging table for x-rays, CT scans, or the like. These constant transfers between different patient support apparatuses can be difficult for the patient, and difficult for caregivers, particularly when the patients are unable to provide any assistance or with heavier patients that are being cared for by smaller caregivers.

Patient support systems and methods designed to overcome one or more of the aforementioned disadvantages are desired.

BRIEF DESCRIPTION OF THE DRAWINGS

FIG. 3 is a perspective view of the patient support deck, transport device, and docking station.

FIG. 3A is a perspective view of an alternative deck section with reinforcing spine structure.

FIGS. 5A and 5B are illustrations of one of the patient support decks engaged by a transport device and capable of translating relative to the transport device.

FIG. 8 is a perspective view of the patient support deck being supported by the docking station with the transport device withdrawing from the docking station.

FIG. 9 is a schematic of an interface between the patient support deck and the docking station or between the patient support deck and the transport device.

DETAILED DESCRIPTION

Figure 1:
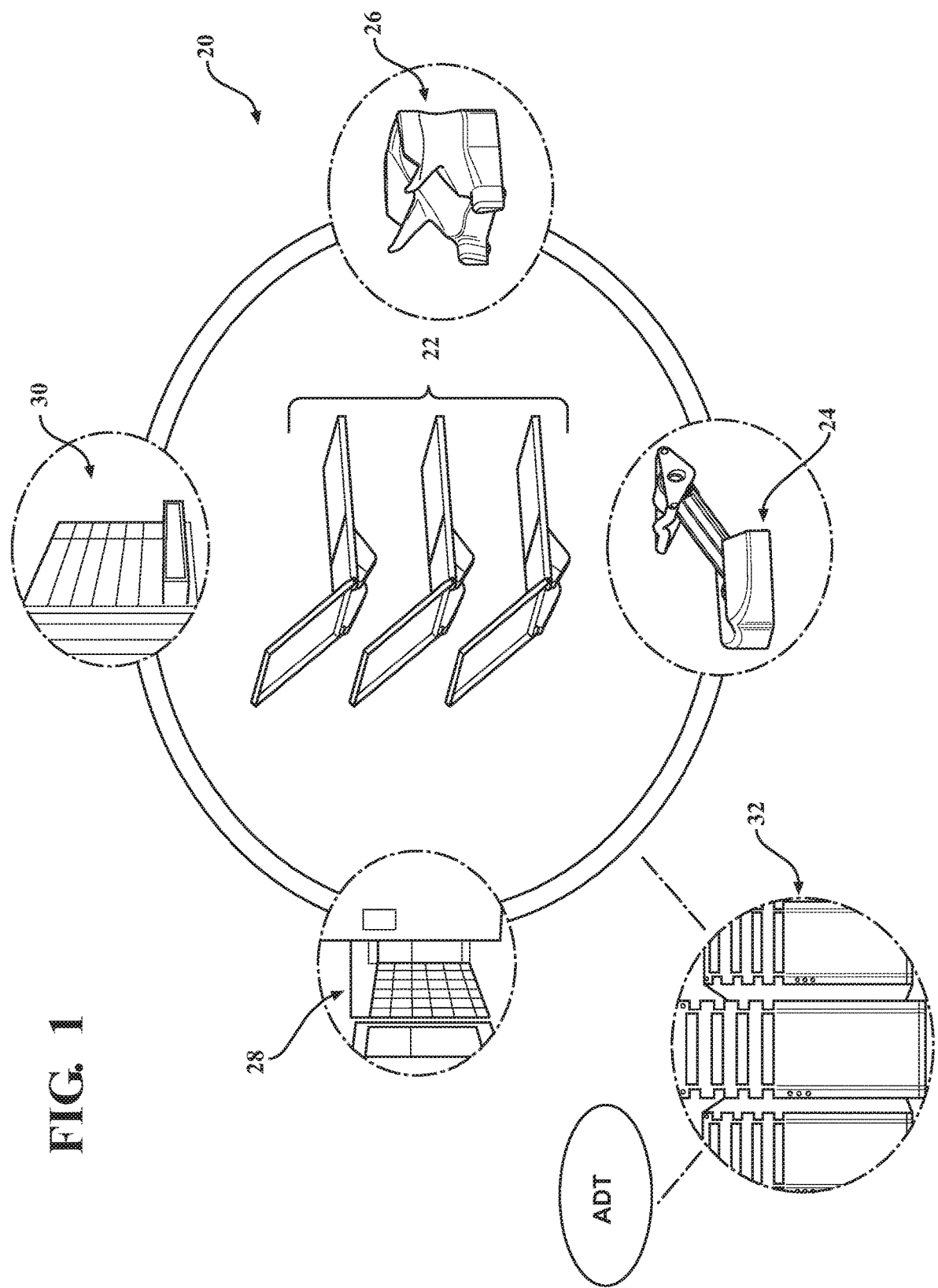
FIG. 1 is an overview of a patient support system that comprises several patient support decks, a transport device, a docking station, a storage facility, a sterilization apparatus, and a control system.
Figure 2:
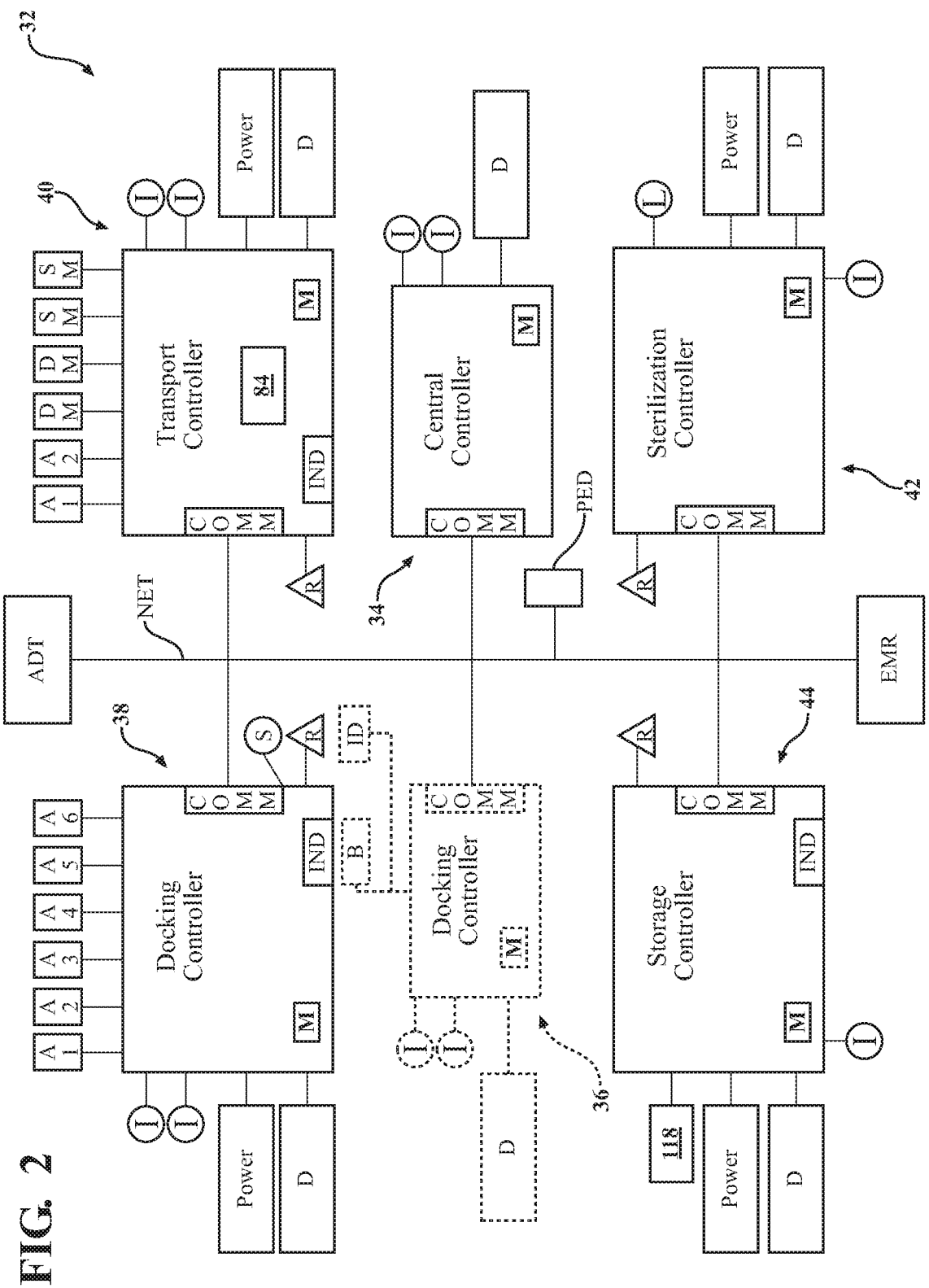
FIG. 2 is a schematic of a control system for connecting a deck controller, a docking controller, a transport controller, a sterilization controller, a storage controller, and a central controller.

Referring to FIG. 1, a patient support system 20 is shown. The patient support system 20 is designed for docking, transporting, sterilizing, and storing patient support decks 22 in a healthcare facility. The patient support system 20 comprises a number of system components to carry out these functions. Docking stations 24 are system components installed at various locations in the healthcare facility, such as in patient rooms, to releasably engage the patient support decks 22 to care for patients. Transport devices 26 are system components adapted to move the patient support decks 22 between locations in the healthcare facility while at the same time maintaining a desired level of care for the patients during transport. Sterilization apparatuses 28 are system components configured to sterilize the patient support decks 22 after use. Storage facilities 30 are system components that store the patient support decks 22 for later retrieval once they are sterilized. A control system 32 is a system component that interconnects each of the other system components so that patient support decks 22, docking stations 24, transport devices 26, sterilization apparatuses 28, and storage facilities 30 can communicate with each other in meaningful ways, as described further below. As shown in FIG. 2, the control system 32 comprises a central controller 34 and one or more deck controllers 36, docking controllers 38, transport controllers 40, sterilization controllers 42, and storage controllers 44 located on a network NET to interconnect the system components, either wired or wirelessly.

The patient support decks 22 are simplified, compared to traditional patient support apparatuses, to ease their docking, transport, sterilization, and storage in the healthcare facility. Traditionally, several different patient support apparatuses may be needed for a single patient during the patient's stay in the healthcare facility. For instance, if the patient is admitted through an emergency department of the healthcare facility, the patient may first be placed on an emergency room stretcher, but then later transferred to a hospital bed in a patient room. Afterward, the patient may need to be transferred from their hospital bed to an imaging table to facilitate imaging, such as x-ray imaging, CT scanning, or the like. Thereafter, the patient will again need to be transferred back to their hospital bed from the imaging table for transport back to their patient room. Transferring patients between such patient support apparatuses can be challenging to caregivers, particularly with heavier patients, and with weak or ill patients unable to provide much assistance in such transfers. The patient support decks 22 described herein provide the advantage of eliminating, or at least limiting, the number of potential transfers needed for a single patient in the healthcare facility. In particular, in some embodiments, the patient support system 20 is designed so that the patient is able to stay on a single one of the patient support decks 22 throughout their stay in the healthcare facility, and in some cases prior to arriving at the healthcare facility. The patient support decks 22 provide this advantage by being modular and being releasably attachable to any of the docking stations and any of the transport devices 26.

The patient support decks 22 are configured to support patients in the health care facility, but without any on-board wheels or powered lift systems. Instead, the wheels for transport are located on the transport devices 26 and lifting/lowering capabilities are provided at the docking stations 24. Further, the patient support decks 22 may lack power sources, movable side rails, and removable headboards or footboards. In some embodiments, the patient support decks 22 lack any electrical components to avoid their degradation during sterilization. Some of the patient support decks 22, in other embodiments, may have limited electronic components such as one of the deck controllers 36, which comprises a communication module COMM for transmitting/receiving signals to/from the other controllers 34, 38, 40, 42, 44 (see FIG. 2) via the network NET, and a battery B. The patient support decks 22 may also comprise a display D in communication with the deck controller 36. The display D may be a touch screen display for receiving user input or other type of display device. In other embodiments, the patient support deck 22 may comprise additional input devices, such as an input device I for generating a transport request signal to request a transport device 26, via the network NET, as described further below, or to issue other commands to the patient support deck 22 or to any of the system components present on the network NET or to retrieve any information available via the network NET. The docking stations 24, transport devices 26, and storage facilities 30 may comprise inductive charging devices IND configured to inductively charge the batteries B of the patient support decks 22 when the patient support decks 22 are engaged by one of the docking stations 24 or transport devices 26 or stored in one of the storage facilities 30. In some cases, the patient support decks 22 may have movable side rails and/or permanent or removable headboards and/or footboards to provide safety barriers for the patients.

As shown in FIG. 2, the patient support decks 22 may have identification devices ID, such as RFID tags, barcodes, or other identification devices that are capable of conveying information relating to the patient support deck 22. Such information can include a type of patient support deck 22, a unique identifier for the patient support deck 22, a weight of the patient support deck 22, a manufacturing date of the patient support deck 22, or the like. The identification devices ID can be read by electronic readers R on the docking stations 24, transport devices 26, sterilization apparatuses 28, and storage facilities 30. Patients can similarly be outfitted with these types of identification devices ID, such as via a bracelet, etc.

In cases where the patient support deck 22 comprises one of the deck controllers 36, such information can be stored in memory M of the deck controller 36 during manufacture, such as non-volatile memory, e.g., EEPROM or NVRAM. Further, in these embodiments, additional information can be entered via one of the input devices I and stored in the memory M at the healthcare facility, such as an identification of the patient assigned to the patient support deck 22, or other data relating to the patient such as patient conditions, special needs of the patient, patient weight, etc. The information provided by the identification device ID and/or the memory M can be utilized by the control system 32 and/or distributed to the docking stations 24, transport devices 26, sterilization apparatuses 28, and/or storage facilities 30, as needed.

Referring to FIG. 3, in the embodiment shown, the patient support deck 22 comprises several deck sections, such as a back section 46, a seat section 48, and a foot section 50. The back section 46 and the foot section 50 are connected to the seat section 48 to articulate between positions relative to the seat section 48. For instance, as shown, the back section 46 and the foot section 50 are pivotally connected to the seat section 48 at pivot joints defining pivot axes P1, P2. The pivot joints can be formed by pivot pins, shafts, and the like. The deck sections 46, 48, 50 provide a patient support surface upon which the patient is supported. The back section 46 and foot section 50 can articulate into several different configurations, including a flat configuration, a chair configuration, and the like.

The deck sections 46, 48, 50 may be reinforced in some cases to support loads on the patient support decks 22. For instance, referring to FIG. 3A, an example of an alternative back section 46a is shown. In this embodiment, the back section 46a comprises a deck 41 fixed to a tube support 43. The tube support 43 is shown being internally corrugated to define a receiving space sized to accommodate a spine structure 45. The spine structure 45 comprises a pair of opposing and elongated spine supports 47.

Compliant members 49 interconnect the spine supports 47. The compliant members 49 as spaced along the length of the spine supports 47. The compliant members 49 are shaped to slide into the receiving space in the tube support 43. By virtue of the corrugated nature of the tube support 43, the receiving space comprises a plurality of channels having geometric shapes configured to receive nodes 51 of the compliant members 49 so that the compliant members 49 are limited from rotating in the tube support 43. The nodes 51 of the compliant members 49 are compliant in a radially inward direction with respect to spine axis SA. The compliant members 49 may be formed of plastic, rubber, or other suitable materials that provide suitable reinforcement to the tube support 43 and consequently to the back section 46a.

In some cases, the back section 46 and foot section 50 are manually adjustable to place the back section 46 and/or foot section 50 into different positions. As a result, no electrical components are needed for their adjustment. In other cases, however, referring to FIG. 4, actuators A1, A2 for articulating the back section 46 and/or foot section 50, respectively, may be provided. In this case, the actuators A1, A2 and/or associated articulating links L1, L2 may be located on the docking stations 24 and/or the transport devices 26. Alternatively, the actuators A1, A2 and/or associated articulating links L1, L2 for moving the back section 46 and/or foot section 50 may be located on the patient support deck 22. In further alternatives, the articulating links L1, L2 may be located on the patient support deck 22, but the actuators A1, A2 maintained on the docking stations 24 and/or the transport devices 26.

By keeping at least the actuators A1, A2 on the docking stations 24 and/or transport devices 26, the patient support decks 22 can be relieved of additional components, reducing their weight and thereby further simplifying docking, transport, sterilization, and storage. In the embodiment shown in FIG. 4, for example, the actuators A1, A2 are located on the docking station 24. The actuators A1, A2 shown are rotary actuators for rotating the articulating links L1, L2, which support the back section 46 and foot section 50. In the embodiment shown, the back section 46 and the foot section 50 are merely resting on the links L1, L2 i.e., without any mechanical interlocking therebetween. Thus, the back section 46 and the foot section 50 are held to the links L1, L2 by virtue of their weight and any weight supported by them. In some embodiments, the back section 46 and foot section 50 may releasably lock to the links L1, L2. In other embodiments, linear actuators or other suitable actuators and/or links or linkages can be provided to enable articulation of the back section 46 and foot section 50. The docking controller 38 is coupled to the actuators A1, A2 in a manner that allows the docking controller 38 to control the actuators A1, A2 when the patient support deck 22 is coupled to the docking station 24. The docking controller 38 may communicate with the actuators A1, A2 via wired or wireless connections to perform one of more desired functions. The actuators A1, A2 are controlled through input devices I (see FIG. 2) on the patient support deck 22 and/or via input devices I (see FIG. 2) located on the docking station 24.

Figure 4:
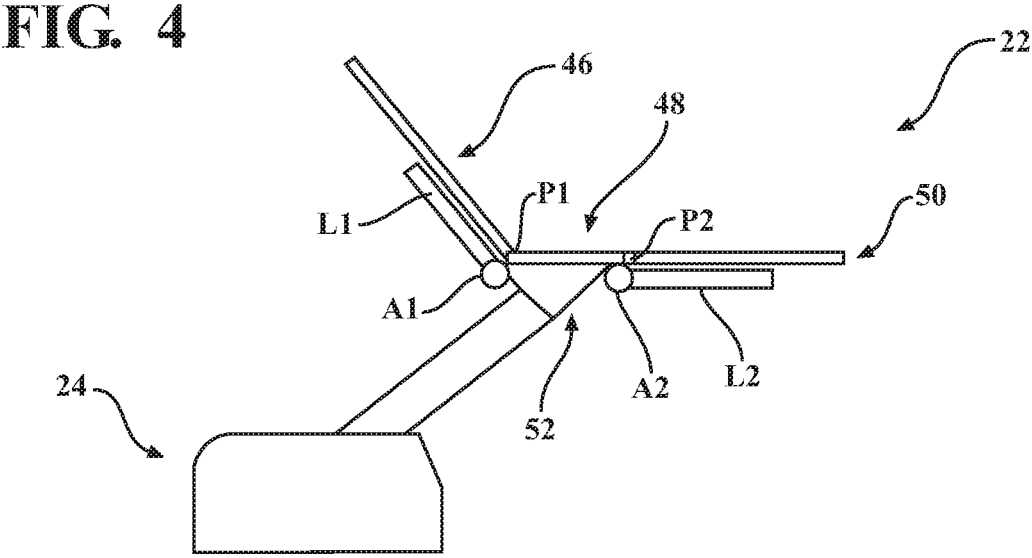
FIG. 4 is an illustration of one of the patient support decks engaged by a docking station having actuators and links for moving deck sections of the patient support deck.

Each of the patient support decks 22 comprise a coupling device 52 configured to be engaged by the docking stations 24 and the transport devices 26 (and in some embodiments the sterilization apparatuses 28 and storage facilities 30). The coupling device 52 may be fixed to the seat section 48 or other location on the patient support deck 22. In some embodiments, the coupling device 52 is a single part, but may comprise multiple parts. The coupling device 52 may lack movable parts and merely facilitate abutting engagement by the docking stations 24 and the transport devices 26, as shown in FIGS. 3 and 4. The patient support decks 22 may be configured to generally be releasably secured to one of a docking station 24, transport device 26, sterilization apparatus 28, or storage facility so that the patient support decks 22 can be accounted for at all times. In some embodiments, the patient support decks 22 are secured via the coupling device 52 or via other engagement mechanisms on the patient support decks 22. In other embodiments, there may be transition periods in which the patient support decks 22 are unsecured during their transition from one station to the next, e.g., from the transport device 26 to the sterilization apparatus 28, but these periods may be short, such as less than 1 minute, less than 30 seconds, less than 5 seconds, and so on.

In the embodiment shown in FIGS. 5A and 5B, the coupling device 52 comprises an upper portion 52a fixed to the seat section 48 and a lower portion 52b configured to be engaged by the docking stations 24 or the transport devices 26, in the manner described below. In this embodiment, the upper portion 52a and the lower portion 52b may be connected by one or more translational joints and/or rotational joints in which the upper portion 52a is able to translate (e.g., slide as shown in FIG. 5B) and/or rotate relative to the lower portion 52b when the patient support deck 22 is connected to the docking stations 24 or the transport devices 26 (shown connected to transport device 26).

This translation could be provided manually or may comprise an actuator 57 between the upper portion 52a and the lower portion 52b. The actuator 57 could be a linear actuator having a housing fixed to the transport device 26. The actuator 57 could engage the upper portion 52a when the patient support deck 22 is mounted to the transport device 26 or the actuator 57 could be part of the patient support deck 22. A drive rod is coupled to the upper portion 52a that translates relative to the housing. Is some cases, the drive rod has a coupling element, such as a hook, detent, snap-fit element, or other type of connection that engages a mating coupling element on the upper portion 52a, such as a loop, detent pocket, snap-fit element, etc. when the patient support deck 22 is mounted to the transport device 26. Other types of actuators are also contemplated. Accordingly, the deck sections 46, 48, 50 are able to translate relative to the docking stations 24 or the transport devices 26, which may be useful for imaging in an imaging device IMDEV (shown in FIGS. 5A and 5B), such as an x-ray imaging device, CT imaging device, MRI imaging device or the like. Likewise, the deck sections 46, 48, 50 may be able to rotate 360 degrees relative to the docking stations 24 or the transport devices 26 via the one or more rotational joints. Some of the patient support decks 22 may also be able to translate and rotate when engaged by the docking stations 24 or transport devices 26 to facilitate easier communication with caregivers and visitors, to facilitate easier ingress and egress, and/or to facilitate easier transfers to other types of patient support decks 22 or patient support apparatuses, such as wheelchairs.

Figure 5C:
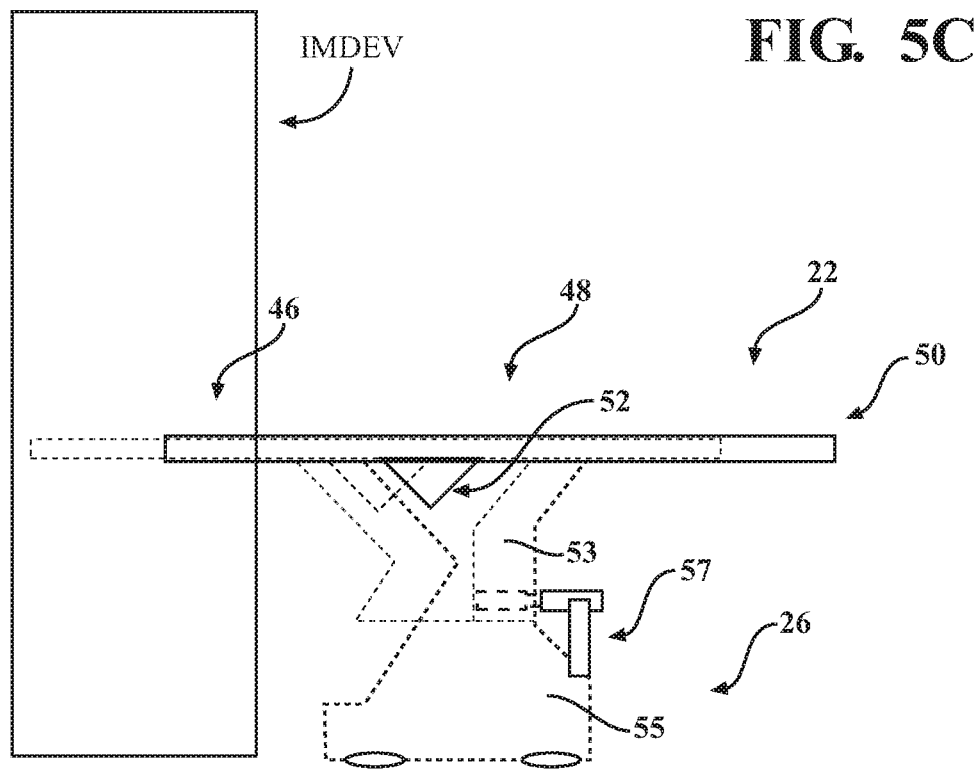
FIG. 5C is an illustration of one of the patient support decks engaged by a transport device in which the transport device has an upper portion translatable relative to a lower portion.

Referring to FIG. 5C, in addition to (or as an alternative to) the patient support deck 22 having the capability of translating relative to the transport device 26, the transport device 26 itself may be capable of translating its own upper portion 53 relative to a lower portion 55 thereof, such as translating the upper portion 53 that engages the patient support deck 22 relative to the lower portion 55 that engages the floor surface. This translation could be provided manually or may comprise an actuator 57 between the upper portion 53 and the lower portion 55. The actuator 57 could be a linear actuator having a housing fixed to the lower portion 55 and a drive rod fixed to the upper portion 53 that translates relative to the housing. Other types of actuators are also contemplated. The upper and lower portions 53, 55 could be slidably coupled by tracks or other mechanisms to allow relative translating movement.

A mattress (not shown) may be disposed on the patient support deck 22 during use. The mattress comprises a secondary patient support surface upon which the patient is supported. The patient support deck 22 has a head end and a foot end corresponding to designated placement of the patient's head and feet on the patient support deck 22. The mattress may be omitted in certain embodiments, such that the patient rests directly on the patient support surface provided by the deck sections 46, 48, 50.

Each of the patient support decks 22 can be differently configured to accommodate patients of different needs. The different configurations of the patient support decks 22 may comprise at least one of different widths, different lengths, different shapes, different weights, different accessories, and the like. For instance, one type of patient support deck 22 may be configured for taller patients by virtue of having a longer back section 46 or foot section 50 than other types of patient support decks 22. One type of patient support deck 22 may be specially configured to accommodate patients that require oxygen or other service. Another type of patient support deck 22 may be configured to have anchors for attaching patient restraining devices in the event the patient is known to be combative. Yet another type of patient support deck 22 may have other integrated accessories such as an egress handle, one or more siderails, a headboard, and/or a footboard. Additionally, some types of patient support decks 22 may comprise one of the deck controllers 36, while other types lack any of the deck controllers 36 and/or any other electrical components. The patient support decks 22, in some cases, can be matched to particular docking stations 24 or transport devices 26. More specifically, a certain type or model of patient support deck 22 may only be compatible with certain docking stations 24 or transport devices 26 that are specifically outfitted to accommodate such patient support decks 22. For instance, one model of patient support decks 22 may be suited for small children and are only usable with docking stations 24 and transport devices 26 also sized and configured to accommodate small children. Similarly, differently configured docking stations 24 and/or transport devices 26 may be provided for the same type/style of patient support decks 22 to provide different functions to the same patient support deck 22.

Figure 6:
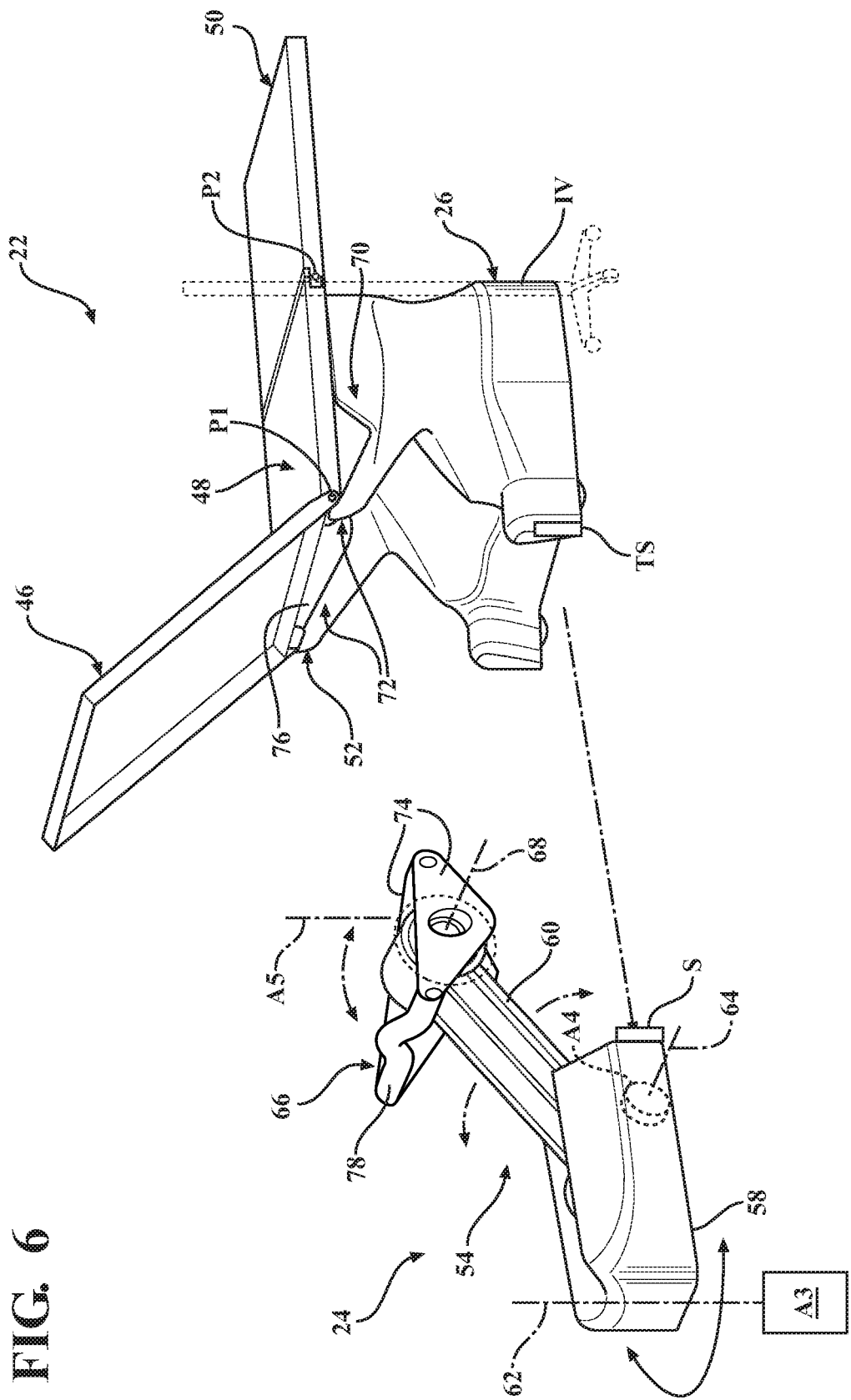
FIG. 6 is a perspective view of the patient support deck being transported by the transport device into proximity of the docking station.
Figure 6A:
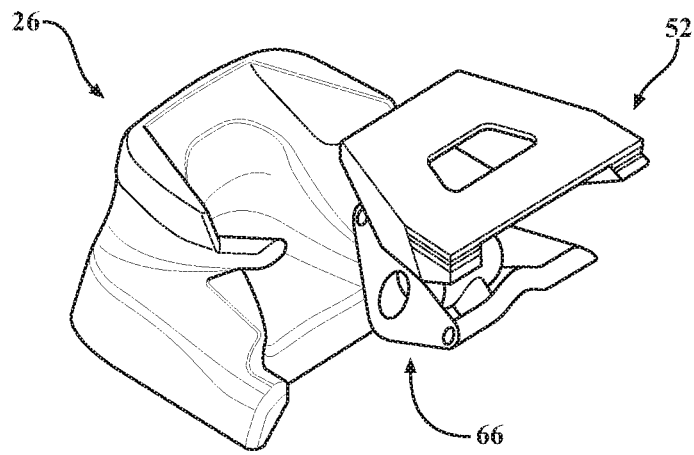
FIGS. 6A through 6C are perspective views illustrating connections between a mounting device of a docking station and a coupling device of a patient support deck.

Referring to FIG. 6, the docking stations 24 are located throughout the healthcare facility. The docking stations 24 are compatible with all of the patient support decks 22 so that any of the patient support decks 22 can be engaged by any of the docking stations 24. The docking stations 24 may be provided in patient rooms, x-ray rooms, intensive care, emergency rooms, or the like. The docking stations 24 may be configured to be floor-mounted or ceiling-mounted (floor-mounted are shown). The docking stations 24 are configured, much like traditional headwalls, to provide one or more services to the patient and/or the patient support deck 22. The docking stations 24 are also configured to move the patient support decks 22 in multiple degrees of freedom, such as lifting/lowering the patient support decks 22, tilting the patient support decks 22, and/or rotating the patient support decks 22.

There may be different types of docking stations 24 in the healthcare facility to provide different levels of services or to provide different features. For instance, if the docking station 24 is located in an x-ray room, then the docking station 24 may be configured to only move in two degrees of freedom, such as one degree of freedom to lift and lower the patient support deck 22 and one degree of freedom to translate the patient support deck 22 into and out of an imaging device IMDEV. Conversely, the docking stations 24 in the patient rooms may be configured so that their manipulators 54 provide at least three degrees of freedom of movement of the patient support deck 22, including, lifting/lowering, tilting (lateral and/or longitudinal) and/or rotating the patient support deck 22 about the docking station 24.

Different docking stations 24 may also be capable of providing different services to the patient support deck 22. For instance, the docking stations 24 may be connected to different combinations of one or more different services provided in the healthcare facility, such as power service, communication service, data service, medical gas service, vacuum service, hydraulic service, low pressure air service, and/or other services. As a result, some of the docking stations 24 may be connected to only a subset of these services, while other docking stations 24 may be connected to all of these services.

The dockings stations 24 comprise sensors S for sensing an approach of the transport devices 26 bringing the patient support decks 22 into proximity of the docking stations 24. Alternatively, or additionally, the sensors S may sense an approach of the patient support decks 22. The sensors S may be proximity sensors responsive to any portion of the transport devices 26 and/or patient support decks 22 being in proximity of the docking station 24 or the sensors S may be receivers responsive to a transmitter TS on the transport devices 26 and/or patient support decks 22, such as RFID tags or other transmitters on the transport devices 26 and/or patient support decks 22 that are able to send a signal to the docking stations 24 when the transport stations 26 and/or patient support decks 22 are within a line-of-sight or other proximity to the docking stations 24. In response to detecting the presence of one of the transport devices 26 and/or patient support decks 22, the docking station 24 may automatically raise or lower, depending on whether the docking station 24 is engaging a new patient support deck 22 (it will lower) or about to release an existing patient support deck 22 (it will be raised). Accordingly, room is made for the transport device 26 to move into position to drop off or pick up the patient support deck 22.

Each of the docking stations 24 comprise a manipulator 54 configured to releasably engage any of the patient support decks 22 once the patient support decks 22 are brought into proximity of the docking station 24. The manipulator 54 comprises a base 58 movable in at least one degree of freedom relative to the floor surface and an arm 60 movable relative to the base 58. The arm 60 may be configured like the tube support 43 shown in FIG. 3A, including a spine structure similar to the spine structure 45.

Actuators A3, A4 move the base 58 and the arm 60. The actuators A3, A4 comprise a base actuator A3 coupled to the base 58 for rotating the base 58 about a rotational axis 62 and an arm actuator A4 coupled to the base 58 for pivoting the arm 60 relative to the base 58 about a pivot axis 64. The base 58 carries the arm 60 and is rotatable with the arm 60 relative to the floor surface about the rotational axis 62. A tilt actuator A5 is coupled to the arm 60 to tilt the patient support deck 22 between Trendelenburg and reverse Trendelenburg positions. In particular, the tilt actuator A5 is coupled to a mounting device 66 of the manipulator 54, which engages the coupling device 52 of the patient support deck 22. The tilt actuator A5 pivots the mounting device 66 about pivot axis 68 during operation. The arm actuator A4 and the tilt actuator A5 can be timed to operate simultaneously so that the manipulator 54 is able to lower the patient support deck 22 while keeping the patient support deck 22 in a constant horizontal orientation. Alternatively, a timing linkage (not shown) may be present between the arm actuator A4 and the mounting device 66 to keep the mounting device 66 horizontal while raising/lowering the arm 60.

The mounting device 66 is located at a distal end of the arm 60. The mounting device 66 is located at the distal end to easily engage patient support decks 22. As previously described, each patient support deck 22 has a coupling device 52 that is adapted to be engaged by the docking stations 24 and the transport devices 26. Referring briefly to FIG. 3, the coupling device 52 of each patient support deck 22 has a first interface 70 for being releasably engaged by the transport devices 26 and a second interface 72 for being releasably engaged by the docking stations 24. The interfaces 70, 72 are provided at separate locations on the coupling device 52 so that the docking stations 24 are able to interface with the coupling devices 52 while the coupling devices 52 remain engaged by the transport devices 26, or vice versa.

Figure 6B:
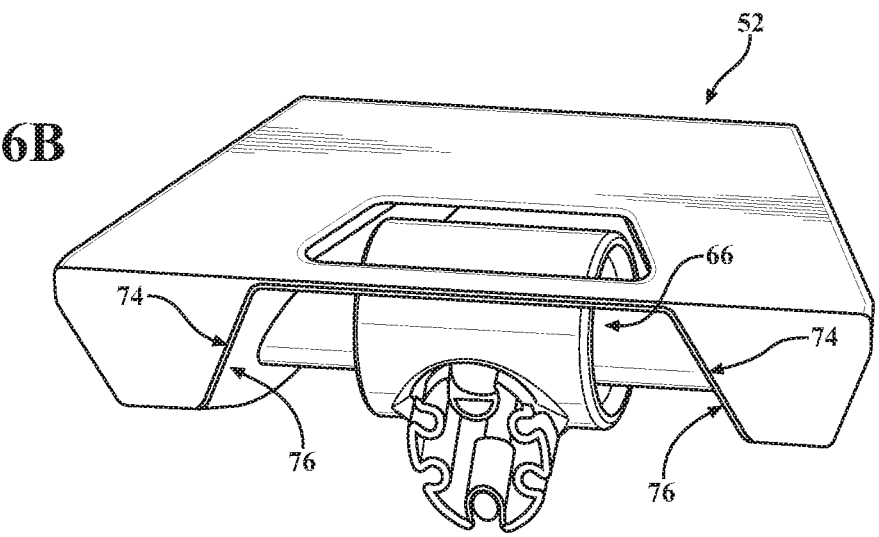
Figure 6C:
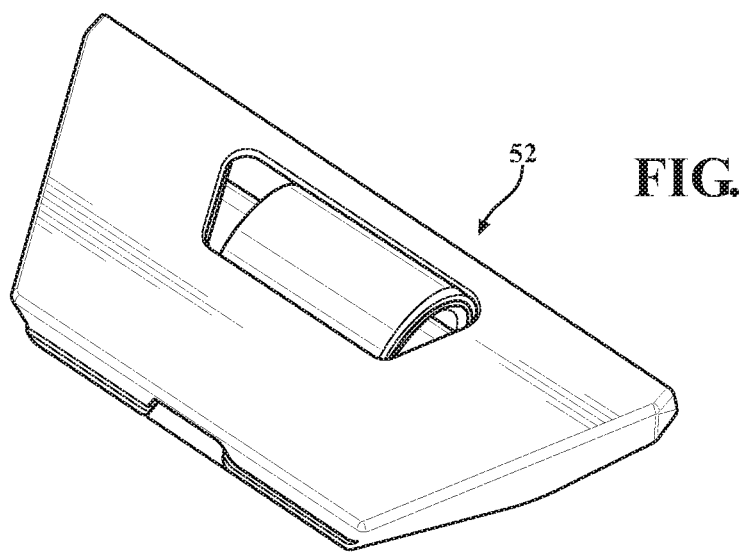
Figure 7:
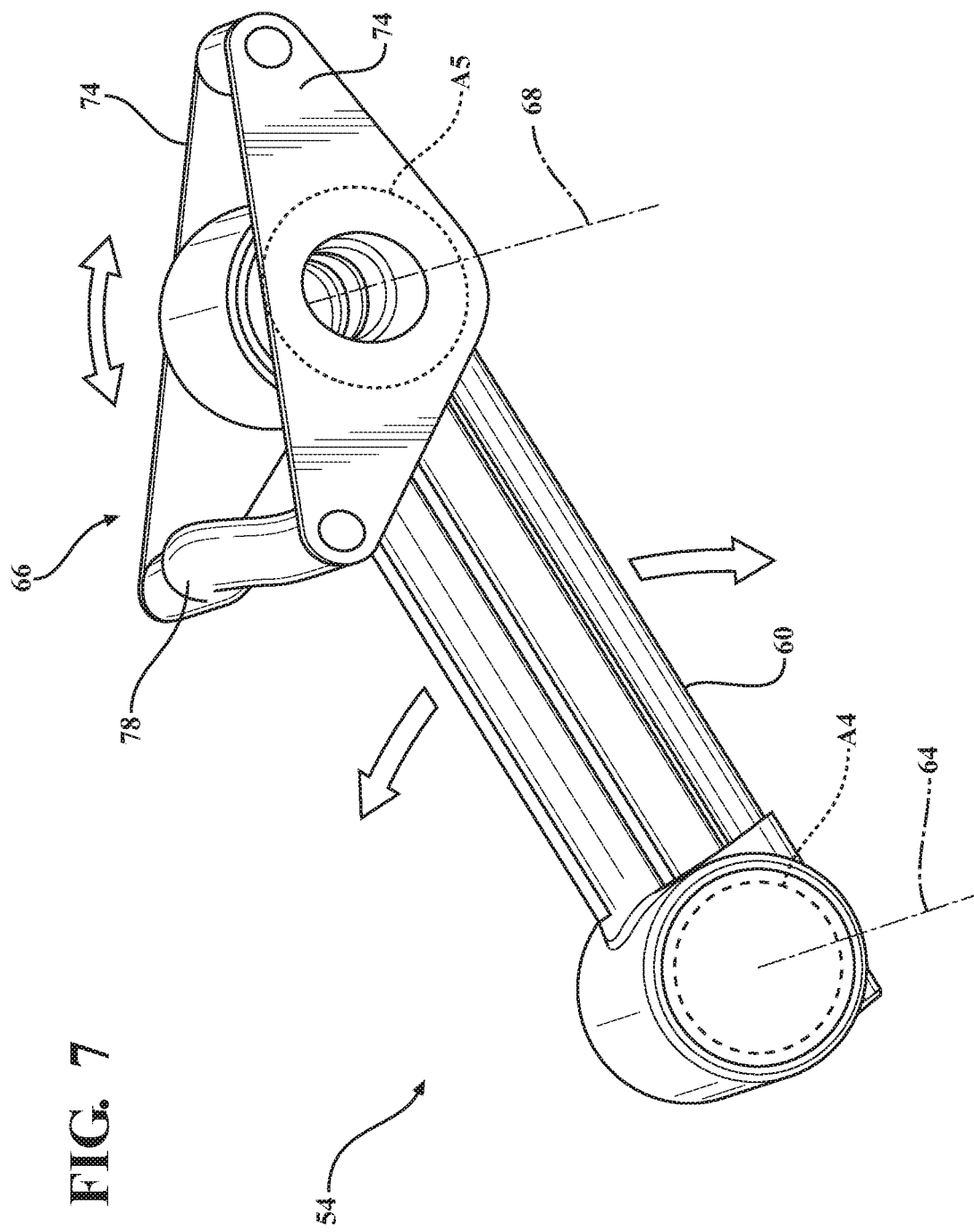
FIG. 7 is a perspective view of an arm of the docking station.

Referring to FIGS. 6 through 7, the mounting device 66 is shaped to mate with the second interface 72 of the coupling device 52. In particular, the mounting device 66 is tapered in shape to ease engagement of the mounting device 66 into the second interface 72. More particularly, the mounting device 66 comprises compound tapers provided by opposed mounting surfaces 74 that taper in two, orthogonal directions, e.g., longitudinally toward the patient support deck 22 in FIG. 6 and vertically upward. The second interface 72 comprises opposed second interface surfaces 76 (see cross-section in FIG. 6B). A receiving space is defined between the second interface surfaces 76. The receiving space is tapered and congruent in shape to the mounting device 66 to receive the mounting device 66 in a self-guiding manner. More specifically, the second interface surfaces 76 are congruent in shape, size, and orientation with the opposed mounting surfaces 74.

Owing to the tapered shape of the mounting device 66 and the second interface 72, once the mounting device 66 engages the second interface 72, the manipulator 54 is able to easily lift the patient support deck 22 off from the transport device 26. Furthermore, the mounting device 66 has a latch 78 that further engages the patient support deck 22 to prevent the patient support deck 22 from sliding off the mounting device 66. In essence, the latch 78 engages in a recess or pocket (not shown) in the patient support deck 22 that prevents longitudinal movement of the patient support deck 22. In some embodiments the coupling device 52 may have the recess or pocket to receive the latch 78 to prevent the coupling device 52 from sliding off the mounting device 66.

Although not shown, the mounting device 66 may comprise movable mounting elements, such as pins that protrude out from the opposed mounting surfaces 74 to further mate with the second interface 72, such as by mating with corresponding bores (not shown) in the second interface 72. Mounting element actuators, such as electronically-controlled solenoids, may be coupled to the mounting elements to move the mounting elements. The mounting elements may be recessed in the mounting device 66 when the patient support deck 22 is unattached and can be configured to be automatically extended in response to the mounting surfaces 74 engaging the second interface surfaces 76, which might be indicated by a contact switch, pressure sensor, or other interface sensor that indicates to the docking controller 38 that the mounting device 66 has engaged the second interface 72. The interface sensor is in communication with the docking controller 38 so that the docking controller 38 activates the mounting element actuators to extend the mounting elements and mate to the second interface 72. The mounting surfaces 74 may also comprise electromagnets that are activated to connect to magnetically attractive portions of the second interface surfaces 76. Thus, the patient support deck 22 can be engaged by the manipulator 54 of the docking station 24 in a touch-free manner, thereby freeing the caregiver to attend to other tasks.

Figure 7A:
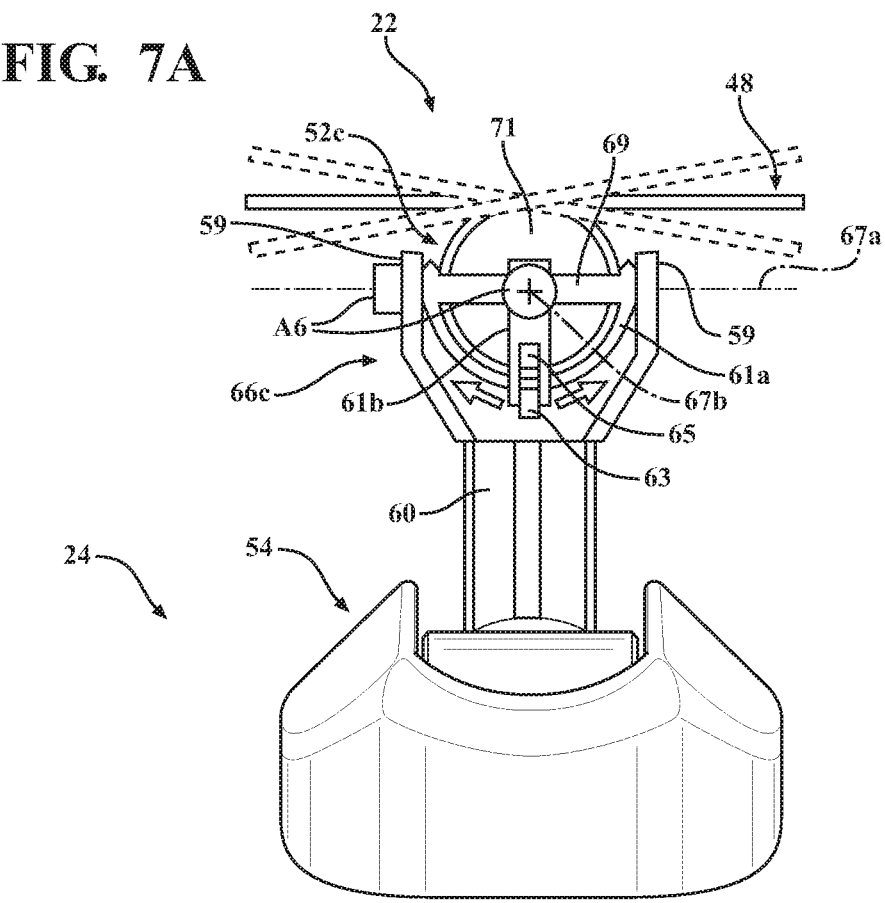
FIG. 7A is an elevational view of an alternative docking station illustrating a ball of a patient support deck seated in a ball-receiving structure of the docking station.
Figure 7B:
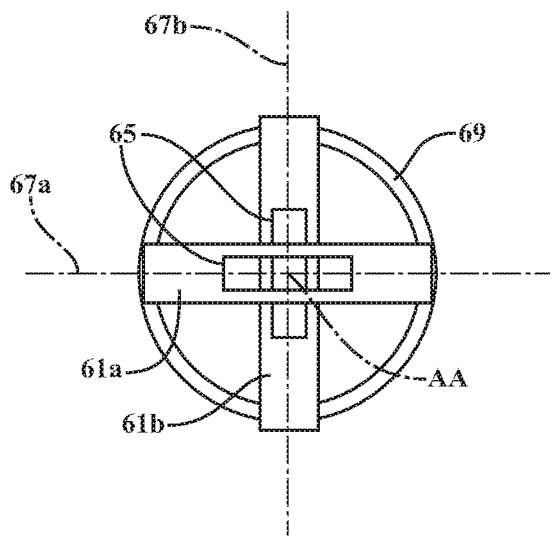
FIG. 7B is a top view of the ball-receiving structure.

Referring to FIGS. 7A and 7B, an alternative coupling device 52c and alternative mounting device 66c are shown. In this embodiment, the coupling device 52c is in the shape of a ball 71 fixed to a bottom of the seat section 48 of the patient support deck 22. The mounting device 66c is configured to accommodate the ball 71. The mounting device 66c comprises a pair of support arms 59 fixed to the arm 60 of the manipulator 54. A ball-receiving structure (top view shown in FIG. 7B) is pivotally supported by the support arms 59 about pivot axis 67a. The ball-receiving structure comprises a collar 69 and a pair of yokes 61a, 61b. The collar 69 is sized to receive the ball 71. The collar 69 is pivotally connected to the support arms 59. Each of the yokes 61a, 61b has an arcuate shape that generally conforms to the shape of the ball 71 to receive the ball 71 in a ball-socket like relationship. One of the yokes 61a is fixed to the collar 69 to move with the collar 69. The other yoke 61b is pivotally supported on the collar 69 about pivot axis 67b to pivot relative to the collar 69 and the yoke 61a, but the yoke 61b also pivots with the yoke 61a when the ball-receiving structure is pivoted about pivot axis 67a.

A post 63 is fixed to a bottom of the ball 71 to be received in slots 65 formed in both of the yokes 61a, 61b. The post 63 is constrained by passing through both of the slots 65, which intersect to form a single aperture AA for the post 63 (see FIG. 7B). In some embodiments, the post 63 has a geometrical shape, such as rectangular, to prevent rotation of the post 63 in the aperture AA. As a result, when the ball-receiving structure is pivoted about pivot axis 67a, then both yokes 61a, 61b simultaneously pivot about pivot axis 67a to move the post 63 so that the patient support deck 22 tilts between various Trendelenburg and reverse Trendelenburg positions. When the yoke 61b is pivoted about the pivot axis 67b relative to the collar 69 and the yoke 61a, then the post 63 is moved in the slot 65 of the yoke 61a so that the patient support deck 22 is tilted in the transverse direction for transverse tilting (see arrows in FIG. 7A) between various transversely tilted positions. Actuators A6 are provided to articulate the ball receiving structure and the yoke 61b about the pivot axes 67a, 67b.

The docking controller 38 controls operation of the manipulator 54. Input devices I in communication with the docking controller 38 can be used to control operation of the manipulator 54, such as by first placing the transport device 26 in a desired location with respect to the docking station 24 and then operating the actuators A3, A4, and/or A5 as necessary to engage the coupling device 52 with the mounting device 66 or to disengage the mounting device 66 from the coupling device 52.

Operation of the manipulator 54 can also be automated to occur in response to the transport device 26 being in proximity to the docking station 24, which can be determined as previously described. For instance, when engaging a new patient support deck 22 being transported by the transport device 26, the manipulator 54 moves the arm 60 autonomously to engage the coupling device 52. The manipulator 54 then controls the arm 60 to lift the patient support deck 22 off from the transport device 26. Similarly, when transferring the patient support deck 22 from the docking station 24 to the transport device 26, the manipulator 54 moves the arm 60 autonomously to lower the patient support deck 22 onto the transport device 26. The manipulator 54 then controls the arm 60 to disengage from the coupling device 52 and return to a "home" or "ready" position in preparation for receiving a new patient support deck 22.

The docking stations 24 may also comprise a display D (see FIG. 2) in communication with the docking controller 38. The display D may be a touch screen display for receiving user input or other type of display device. In other embodiments, the docking stations 24 may comprise additional input devices, such as an input device I (see FIG. 2) for generating a transport request signal to request a transport device 26, via the network NET, as described further below, or to issue other commands to the docking station 24 or to any of the system components present on the network NET or to retrieve any information available via the network NET. Input devices I may comprise user input devices that allow a user to input commands for the docking station 24, such as commands to control movement of the manipulator 54 via the actuators A3, A4, A5, commands to control operation of the actuators A1, A2 to move the back section 46 or foot section 50, or commands to control any of the services provided by the docking stations 24.

A weigh scale may be provided on the docking station 24 to facilitate the determining and tracking of a patient's weight during their stay in the medical facility. In one embodiment, one or more load cells may be placed on the mounting device 66 in order to measure a weight of the patient support deck 22, along with the patient, on the manipulator 54. The load cells communicate with the docking controller 38, either by wire or wirelessly. By virtue of the identification device ID on the patient support deck 22, the docking station 24 is able to retrieve a stored weight of the patient support deck 22, which is information coded in the identification device ID, information that has been manually or otherwise entered and stored in the memory M of the deck controller 36, and/or information otherwise stored in the control system 32. By knowing the weight of the patient support deck 22, the weight of the patient can be deduced by the docking controller 38 and saved in the patient's electronic medical record EMR or in another location in the control system 32.

Figure 8A:
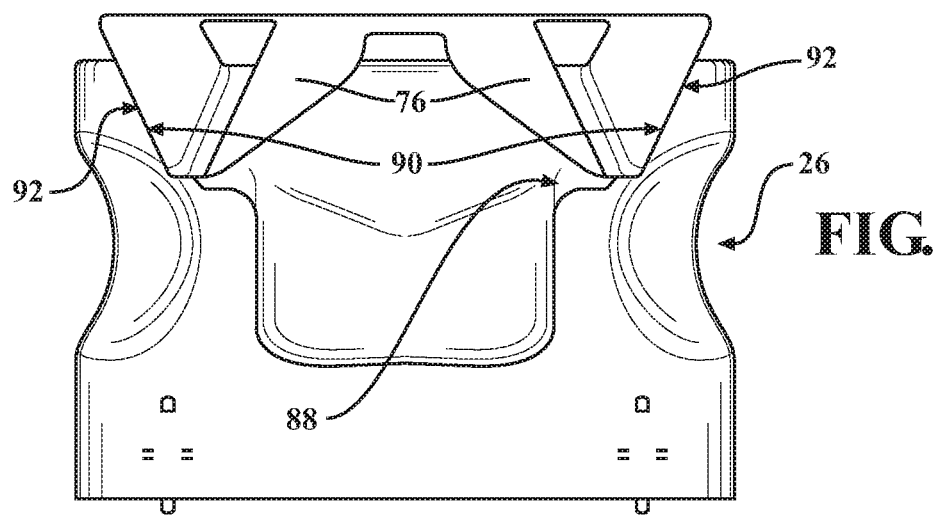
FIG. 8A is a cross-sectional view illustrating a connection between the coupling device of the patient support deck and a cradle of a transport device.
Figure 8B:
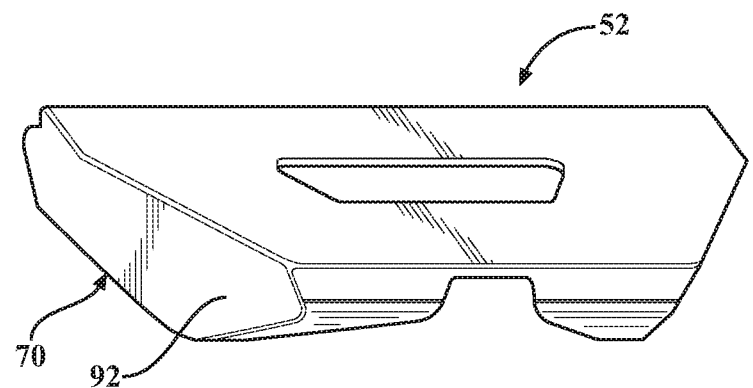
FIG. 8B is a perspective view of the coupling device.

Referring to FIG. 8, the transport devices 26 are movable across floor surfaces to transport the patient support decks 22 between locations, such as between patient rooms, from an x-ray room to a patient room, or the like. Similar to the docking stations 24, the transport devices 26 are configured to releasably engage the patient support decks 22 to carry the patient support decks 22 for transport. Each transport device 26 comprises a support structure 80 that is configured to support the patient support decks 22, with either a patient present on the patient support deck 22 or absent from the patient support deck 22. There may be several different types of transport devices 26 available in any single healthcare facility. The transport devices 26 may differ based on size, configuration, support services, etc. During transport, the patient support decks 22 may be arranged in many different configurations, including chair configuration, fully flat configurations, and the like.

When patients are being moved with the patient support deck 22, the transport devices 26 are intended to maintain a desired level of care for the patients during transport. As a result, some of the transport devices 26 may be equipped much like traditional headwalls, to provide one or more services to the patient and/or the patient support deck 22, such as power service, communication service, data service, medical gas service, vacuum service, hydraulic service, low pressure air service, and/or other services. Accordingly, the transport devices 26 may have on-board battery power, communication and data connections, medical gas service (e.g., small oxygen bottle), vacuum pump, hydraulic unit, low pressure air compressor, or other sources of service for transport. The transport device 26 may also comprise an on-board defibrillator in some embodiments. Further, as shown in hidden lines in FIG. 6, an IV pole clamp and arm may extend from the transport device 26 to carry an IV pole along with the patient support deck 22 between locations.

Returning to FIG. 8, wheels 82 are coupled to the support structure 80 to provide mobility to the transport device 26. The wheels 82 may comprise combinations of swiveling caster wheels, non-swiveling wheels, powered wheels, non-powered wheels, steerable wheels, non-steerable wheels, and the like. In the embodiment shown, two of the wheels 82 are powered, non-swiveling wheels and two of the wheels 82 are non-powered, steerable wheels. Driving devices, such as drive motors DM and steering motors SM (see FIG. 2) are coupled to the powered wheels and the steerable wheels. Accordingly, the transport device 26 can be driven via an input device I (see FIG. 2) on the transport device 26. The transport device 26 could also be driven remotely by a remote input device, such a portable electronic device. Such remote driving could be facilitated by one or more cameras (not shown) on the transport device 26 that can be viewed by an operator on the portable electronic device while the operator drives and steers the transport device 26 via commands using the portable electronic device. Alternatively, the transport device 26 can be autonomously controlled by the transport controller 40, which can autonomously control operation of the drive motors DM and the steering motors SM to move between locations in response to a transport request signal. The transport device 26 is operable to autonomously drive into proximity of the docking stations 24, sterilization apparatuses 28, and storage facilities 30 to deliver/retrieve the patient support decks 22 to/from the docking stations 24, sterilization apparatus 28 and storage facilities 30. One example of an autonomous driving system that could be utilized is shown in U.S. Provisional Patent Application No. 62/182,911, entitled "Patient Support Apparatuses With Navigation And Guidance Systems," filed on Jun. 22, 2015, hereby incorporated by reference.

In the embodiment shown, the support structure 80 of the transport device 26 comprises a seat portion 84 and a back portion 86. The support structure 80 may further comprise an internal support frame (not shown) for supporting the seat portion 84 and the back portion 86. In some embodiments, the seat portion 84 and the back portion 86 may be adjustable to suit each patient. Actuators (not shown) may be provided, for example, to adjust a height of the seat portion 84 and an angle of the back portion 86. The seat portion 84 and the back portion 86 enable the transport device 26 to operate as a wheelchair when disengaged from the patient support decks 22. This may be useful, for instance, if the docking station 24 is configured to monitor the patient in order to determine if the patient is preparing to exit the patient support deck 22. As a result, if a bed exit is determined to be imminent, the docking station 24 may be configured to generate a transport request signal to call one of the transport devices 26 to the patient so that the patient can be moved by the transport device 26 as desired, using the transport device 26 as a wheelchair. Further, owing to the drivable/steerable nature of the wheels 82, the patient may be able to control movement of the transport device 26 via the transport controller 40 using one of the input devices I, such as a control lever or other input device for driving and steering the transport device 26. The transport device 26 may also be utilized to assist the patient with egress from the patient support deck 22 and could be employed as a walker or early mobility assistant for the patient.

Figure 8C:
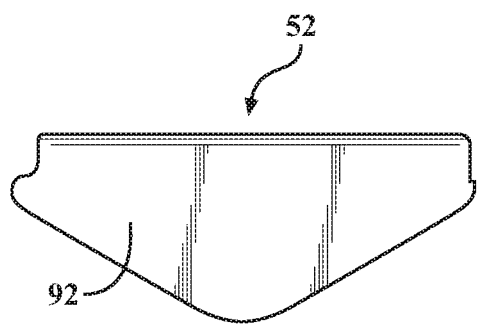
FIG. 8C is a side elevational view of the coupling device.

In the embodiment shown in FIGS. 8 through 8C, the transport device 26 comprises a cradle 88 shaped to mate with the first interface 70. The cradle 88 comprises opposed cradle surfaces 90 (only one seen in FIG. 8) and the first interface 70 comprises opposed first interface surfaces 92 (only one seen in FIG. 8) shaped to engage the opposed cradle surfaces 90 (see FIG. 8A). The cradle 88 is shaped to simply receive in an abutting manner, the coupling device 52 of the patient support deck 22 so that the coupling device 52 is prevented from sliding relative to the transport device 26. The transport device 26 may comprise other features for releasably coupling to the patient support decks 22. The first interface 70 is configured such that the first interface surfaces 92 are automatically separated from the cradle surfaces 90 upon the mounting device 66 of the manipulator 54 engaging the second interface surfaces 76 and then lifting the patient support deck 22 off the transport device 26. Similarly, the first interface surfaces 92 automatically abut the cradle surfaces 90 upon the mounting device 66 lowering the patient support deck 22 onto the transport device 26 when transferring the patient support deck 22 from the docking station 24 to the transport device 26. In the embodiment shown, the cradle 88 is shaped to support the patient support deck 22 and constrain the coupling device 52, and by extension the patient support deck 22, from tilting and from any translational or rotational movement, except that such movement may be provided by separate joints of the coupling device 52 as shown in FIGS. 5A and 5B. In other embodiments, the transport device 26 may be configured to allow such movement. For example, the transport device 26 may comprise the separate upper portion 53 with the cradle 88 wherein the upper portion 53 is able to tilt, translate, or rotate, relative to the lower portion 55 comprising the wheels 82.

The cradle 88 may comprise movable mounting elements (not shown), such as pins that protrude out from the opposed cradle surfaces 90 to further mate with the first interface 70, such as by mating with corresponding bores (not shown) in the first interface 70. Mounting element actuators, such as electronic solenoids, may be coupled to the mounting elements to move the mounting elements. The mounting elements may be recessed in the cradle 88 when the patient support deck 22 is unattached and can be configured to be automatically extended in response to the first interface surfaces 92 engaging the cradle surfaces 90, which might be indicated by a contact switch, pressure sensor, or other interface sensor that indicates to the transport controller 40 that the first interface 70 has engaged the cradle 88. The interface sensor is in communication with the transport controller 40 so that the transport controller 40 activates the mounting element actuators to extend the mounting elements and mate to the first interface 70. The cradle surfaces 90 may also comprise electromagnets that are activated to connect to magnetically attractive portions of the first interface surfaces 92. Thus, the patient support deck 22 can be engaged by the transport device 26 in a touch-free manner, thereby freeing the caregiver to attend to other tasks.

A weigh scale may be provided on one or more of the transport devices 26 to determine a patient's weight. In one embodiment, one or more load cells may be placed on the cradle 88 in order to measure a weight of the patient support deck 22, along with the patient, on the transport device 26. The load cells communicate with the transport controller 40, either by wire or wirelessly. By virtue of the identification device ID on the patient support deck 22, the transport device 26 is able to retrieve a stored weight of the patient support deck 22, which is either information coded in the identification device ID, or information that has been manually or otherwise entered and stored in the memory M of the deck controller 36 or otherwise stored in the control system 32. By knowing the weight of the patient support deck 22, the weight of the patient can be deduced by the transport controller 40 and saved in the patient's electronic medical record EMR or in another location in the control system 32. The weigh scale could also be located on the patient support deck 22 is some embodiments.

As shown in FIG. 2, the transport controller 40 controls operation of the transport device 26. Input devices I in communication with the transport controller 40 can be used to control operation of the transport controller 40. Operation of the transport device 26 can also be automated as previously described. The transport devices 26 may also comprise a display D in communication with the transport controller 40. The display D may be a touch screen display for receiving user input or other type of display device. In other embodiments, the transport devices 26 may comprise additional input devices, such as an input device I for generating a transport request signal to request a transport device 26 (in case the current transport device 26 is disabled), via the network NET, as described further below, or to issue other commands to the transport device 26 or to any of the system components present on the network NET or to retrieve any information available via the network NET. Input devices I may comprise user input devices that allow a user to input commands for the transport devices 26, such as commands to control operation of the actuators A1, A2 to move the back section 46 or foot section 50, or commands to control any of the services provided by the transport devices 26. Such input devices I may issue commands either wired or wirelessly.

Referring to FIG. 9, interface connections between the patient support decks 22 and the docking stations 24 or between the patient support decks 22 and the transport devices 26 are shown. These interface connections are intended to provide the patient support decks 22 with continuous services while docked and during transport, such as power service, communication service, data service, medical gas service, vacuum service, hydraulic service, low pressure air service, and/or other services. Such services are provided either through the docking station 24, which acts much like a conventional headwall by virtue of being fixed in a patient room or other location, or through the transport device 26 responsible for transporting the patient support deck 22. When the patient support deck 22 is engaged with the docking stations 24, these interface connections are made between the docking station 24 and the patient support deck 22. However, when the patient support deck 22 is removed from the docking station 24 and carried by the transport device 26, then the transport device 26 seamlessly accommodates the same connections.

Couplings 94 on the patient support deck 22 are configured to be connected to mating couplings 96 on the docking station 24 or mating couplings 98 on the transport device 26. In one embodiment, the couplings 94 are located on the interfaces 70, 72 to automatically connect to the mating couplings 96 on the mounting device 66 or the mating couplings 98 on the cradle 88 when the patient support deck 22 is engaged by the docking station 24 or the transport device 26. This enables an automatic and touch-free connection of at least one of the data service, the communication service, the power service, the medical gas service, the vacuum service, the hydraulic service, the pressurized air service, and other services from the docking station 24 or the transport device 26 to the patient support deck 22 upon engagement of the patient support deck 22 by the docking station 24 or the transport device 26.

Side rails (not shown) may be provided by the docking station 24 or the transport device 26 or could be coupled to the patient support deck 22. The side rails could be fixed or movable. One or more side rails may be provided, or in some cases, no side rails are provided. The side rails may be movable between a raised position in which they block ingress and egress into and out of the patient support deck 22, one or more intermediate positions, and a lowered position in which they are not an obstacle to such ingress and egress. Similarly, a headboard or footboard may be provided by the docking station 24 or the transport device 26, or may be present on the patient support deck 22. In other embodiments, no headboard or footboard are provided.

Figure 10:
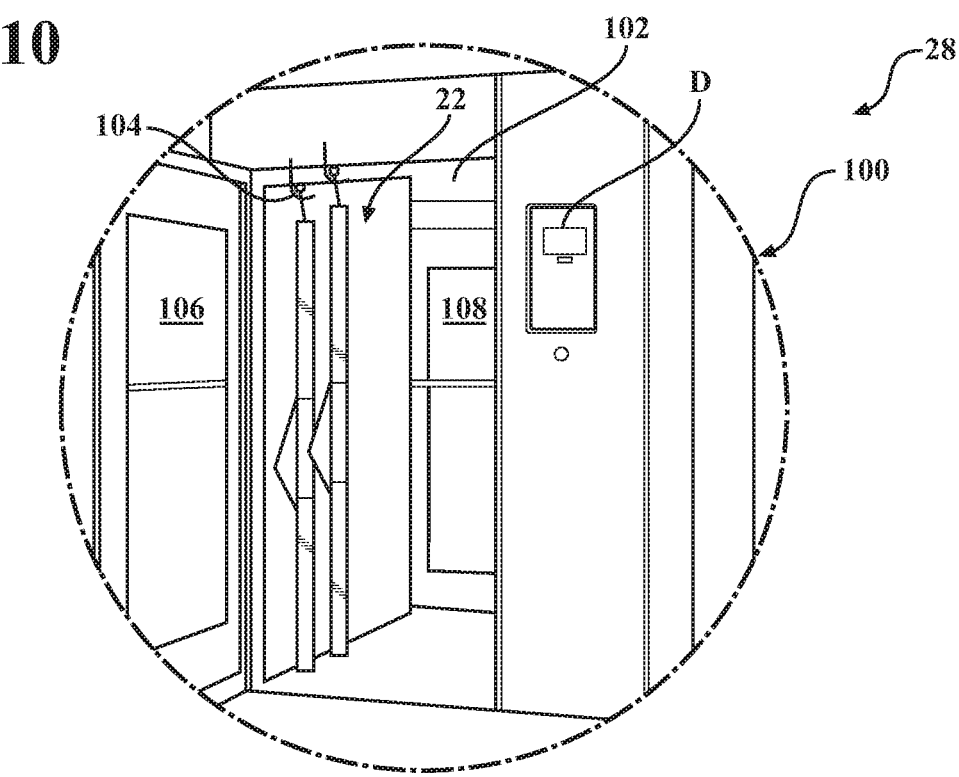
FIG. 10 is a perspective view of the sterilization apparatus.

Referring to FIG. 10, the sterilization apparatus 28 is sized to sterilize at least one patient support deck 22 at a time or may be sized to accommodate multiple patient support decks 22 for simultaneous sterilization. In particular, the sterilization apparatus comprises an enclosure 100 with a chamber 102 sized to receive one or more of the patient support decks 22 for sterilization, without any persons present in the chamber 102. The chamber 102 is sealable to sterilize the one or more of the patient support decks 22 using a sterilization medium, such as ethylene oxide gas, gamma radiation, hydrogen peroxide, or steam.

In some cases, the sterilization apparatus 28 is configured to suspend the one or more of the patient support decks 22 in the chamber 102 off a floor of the enclosure 100, using suspending devices 104, such as racks or hooks (as shown). The sterilization controller 42 controls operation of the sterilization apparatus 28, including sterilization cycles, such as time and frequency of such cycles, controls opening and closing of access doors 106, 108 of the sterilization apparatus 28 which may be operable via electronic locks L in communication with the sterilization controller 42. A display D in communication with the sterilization controller 42 may be located on the enclosure 100, as shown in FIG. 10. The display D may be a touch screen display for receiving user input or other type of display device. In other embodiments, the sterilization apparatus 28 may comprise additional input devices, such as an input device I for generating a transport request signal to request a transport device 26, via the network NET, as described further below, or to issue other commands to the sterilization apparatus 28 or to any of the system components present on the network NET or to retrieve any information available via the network NET.

As previously described, couplings 94 on the patient support deck 22 may be provided so that the docking stations 24 and/or transport devices 26 can provide certain services to the patient support deck 22. Prior to sterilization, ports through which these couplings 94 are accessible may be manually covered with covers (not shown), or covers may be biased into covered positions by biasing devices (not shown), that cover the ports when the couplings 94 are disengaged from the couplings 96 on the docking station 24 or the couplings 98 on the transport device 26. Other components of the patient support decks 22 may be manually or automatically covered prior to sterilization to protect these components. The covers could be actuated based on proximity of the patient support deck 22 to the sterilization apparatus 28, i.e., the transport device 26 could be configured to automatically actuate the covers (via actuators such as electronic solenoids) to cover the ports or other sensitive equipment once the transport device 26 detects being within a predefined proximity to the sterilization apparatus 28 or the sterilization chamber.

In other embodiments, the sterilization components described herein could be replaced by components for disinfecting, sanitizing, or otherwise preparing the patient support decks 22 for subsequent use, e.g., the sterilization apparatuses could be replaced by disinfection apparatuses that operate in the same way, but with potentially different medium being used on the patient support decks 22. Thus, it is contemplated that the patient support decks 22 may be sterilized, disinfected, or otherwise prepared for subsequent use using some form of cleaning medium.

Figure 11:
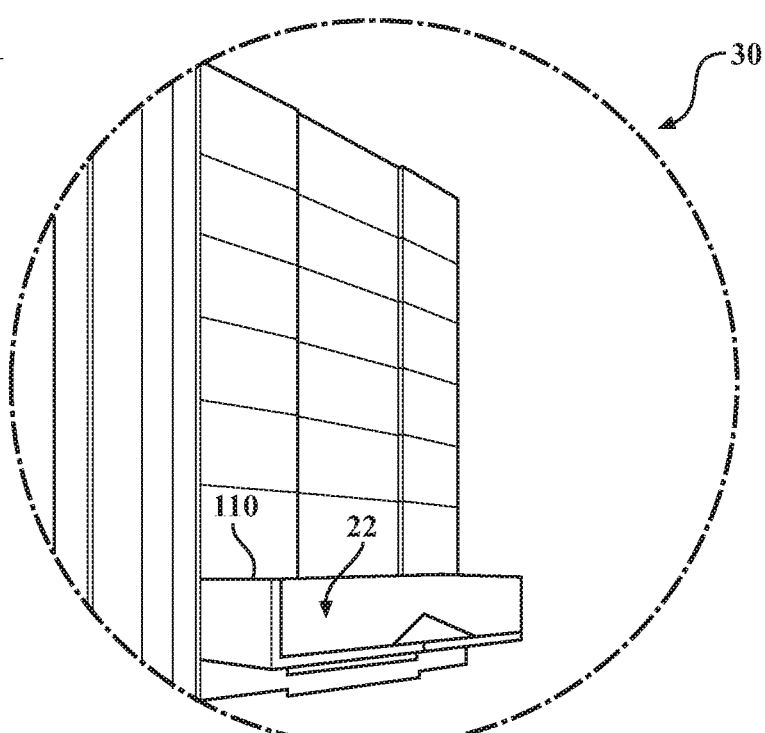
FIG. 11 is a perspective view of a horizontal storage facility.
Figure 12:
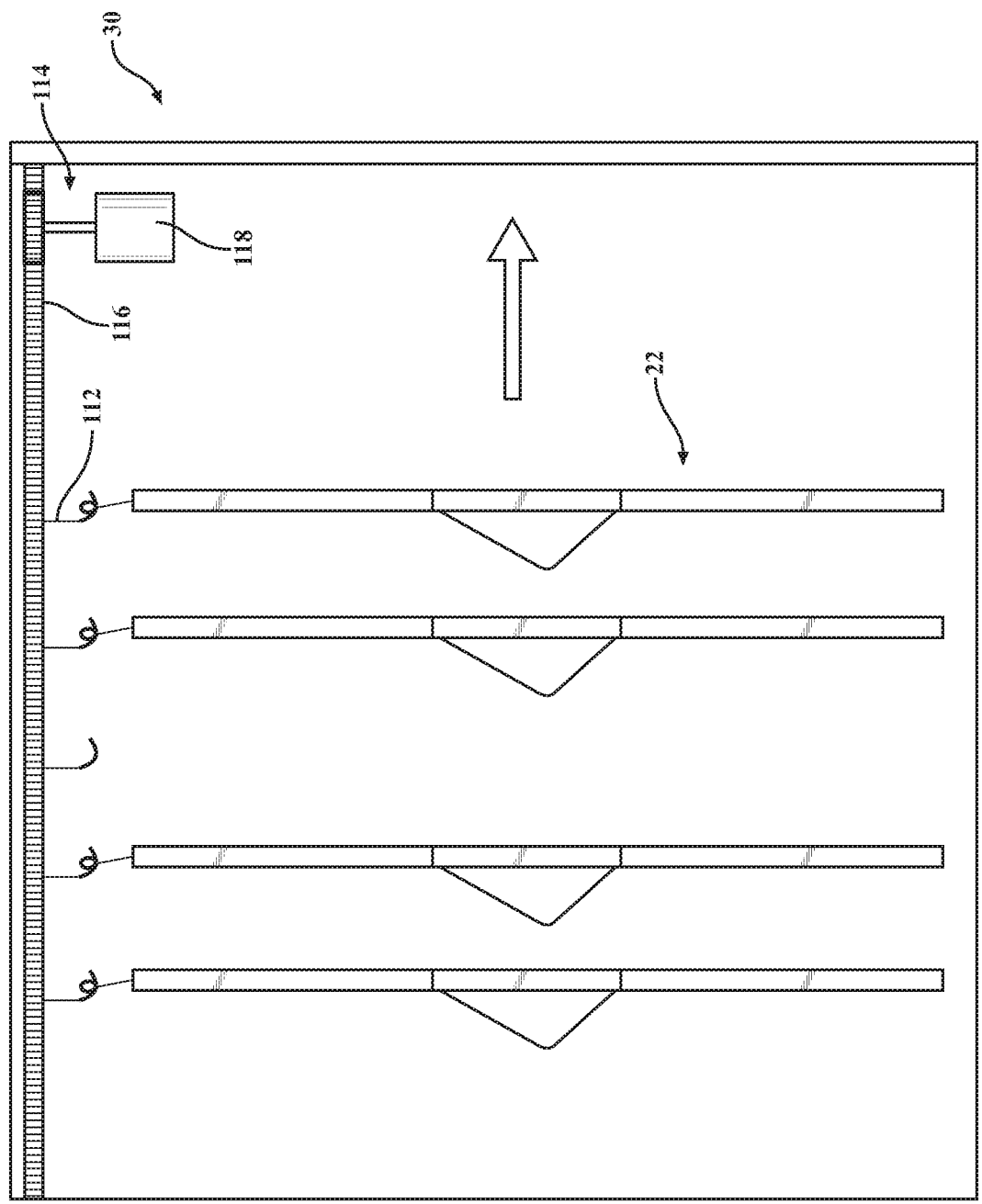
FIG. 12 is an elevational view of a vertical storage facility.

Referring to FIGS. 11 and 12, once a patient support deck 22 is sterilized, it is ready for use by a patient or can be transported by the transport device 26 to one of the storage facilities 30. Each storage facility 30 is sized to house one or more of the patient support decks 22 after they have been sterilized in the sterilization apparatus 28. The storage facilities 30 can store the patient support decks 22 in any organizational manner, such as by stacking the patient support decks 22 on horizontal racks or hanging the patient support decks 22 vertically on hooks. In the embodiment shown in FIG. 11, the storage facility 30 has a stack of slidable storage racks 110 (shown as slidable drawers) for horizontally storing each of the patient support decks 22. The storage racks 110 define storage locations for the patient support decks 22. The storage facilities 30 may also be configured to arrange the patient support decks 22 by type, size, etc. so that storage and retrieval of the patient support decks 22 is optimized.

In another embodiment, shown in FIG. 12, the storage facility 30 comprises hooks 112 that provide storage locations for vertically storing each of the patient support decks 22. Further, the storage facility 30 shown in FIG. 12 comprises an automated retrieval mechanism 114 for retrieving the patient support decks 22. The automated retrieval mechanism 114 comprises a conveyance 116, e.g., belt or chain, from which the patient support decks 22 hang via the hooks 112. A drive motor 118 is operatively connected to the conveyance 116 to drive the conveyance 116 and move the hooks 112, and by extension the patient support decks 22, toward an entrance of the storage facility 30 to retrieve the patient support decks 22, much like how articles of clothing are retrieved at a dry cleaning facility. The storage facilities 30 may be lockable or sealable to prevent unauthorized entry and to maintain a certain level of sterility of the patient support decks 22. Additionally, or alternatively, the patient support decks 22 may be covered in shrink wrap film or stored in other containers in the storage facilities 30 to maintain their sterility. The patient support decks 22 could be contained in such containers during the sterilization process or could be covered in the film after sterilization.

Services may also be provided to/from the patient support decks 22 at their storage locations in the storage facilities 30. In this case, one or more interface connections between the patient support decks 22 and the storage facilities 30 may be provided. These interface connections are intended to provide the patient support decks 22 with services while in storage, such as power service, communication service, data service, medical gas service, vacuum service, hydraulic service, low pressure air service, and/or other services. When the patient support deck 22 is engaged at the storage location, these interface connections are made between an interface at the storage location and the patient support deck 22. However, when the patient support deck 22 is removed from the storage facility 30 and carried by the transport device 26, then the transport device 26 seamlessly accommodates the same connections, or different connections as desired. The interface connections between the patient support decks 22 and the docking stations 24, transport devices 26, and/or the storage facilities 30 may be accomplished in many different ways. For instance, each patient support deck 22 may have only a single coupling that is designed to accommodate multiple types of service connections, e.g., data and power. Similarly, each patient support deck 22 may have several couplings, but only selective ones of the couplings are usable by certain docking stations 24, transport devices 26 and/or storage facilities 30. Further, each patient support deck 22 may have a fixed number of couplings that provide services to the patient support deck 22, but the types of services provided through these fixed number of couplings differs depending on what is connected to the patient support deck 22. For example, the patient support deck 22 may have two couplings through which gas and power are provided when connected to the docking station 24, but through which vacuum and data are provided when connected to the storage facilities 30.

Figure 13:
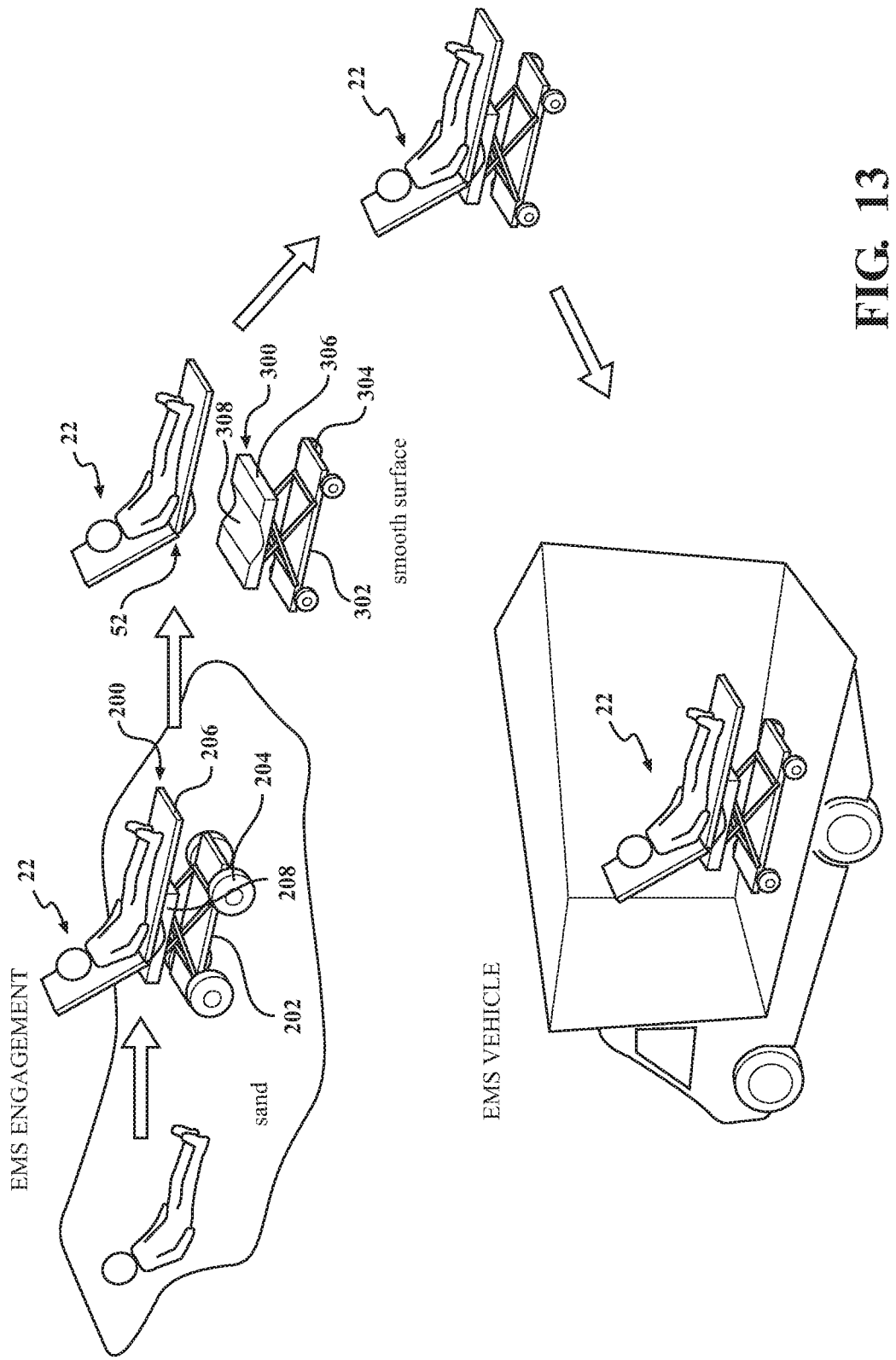
FIGS. 13-15 are illustrations of patient flow from engagement by emergency medical services until discharge and patient support deck flow from engagement by emergency medical services to discharge.
Figure 14:
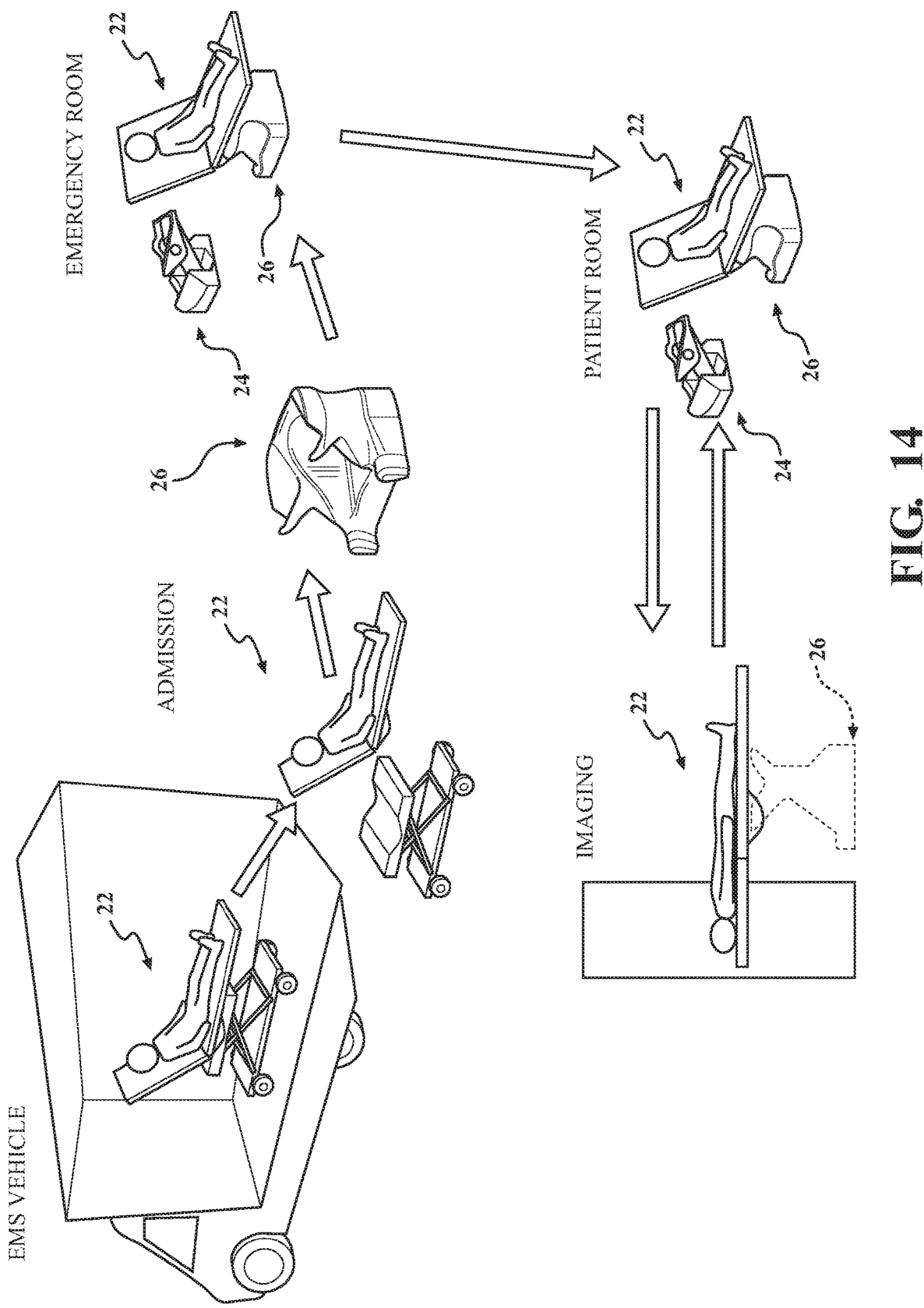
Figure 15:
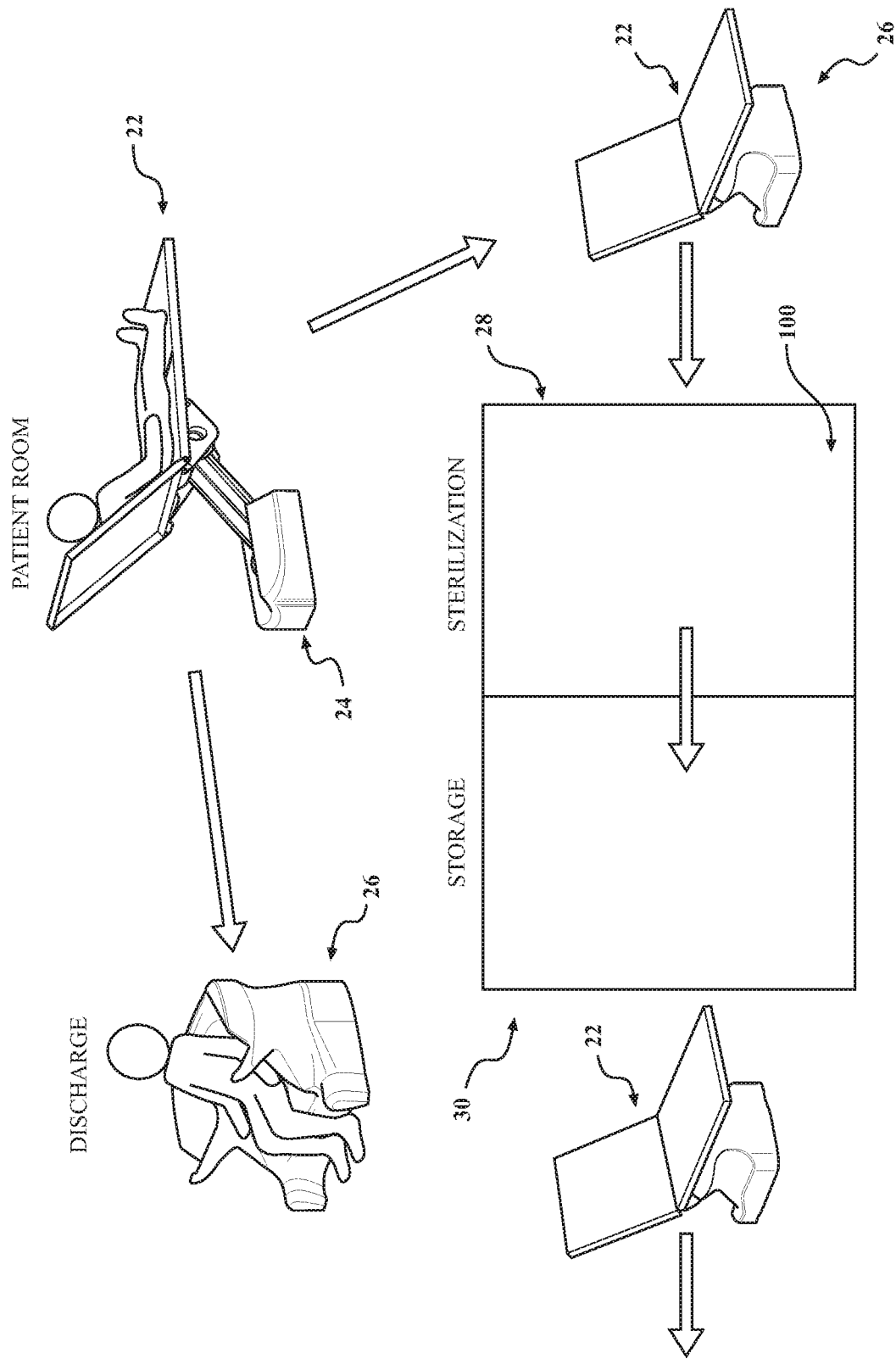

Referring to FIGS. 13 through 15, the flow of a typical patient with respect to the healthcare facility is shown, as well as the utilization, transport, sterilization, and storage of a patient support deck 22 associated with the patient. Referring first to FIG. 13, the patient is first engaged by emergency medical services (EMS) in response to an accident or injury sustained while participating in recreational activities at the beach. As a result, a conventional wheeled stretcher is unable to be easily transported across the sand with the patient supported thereon. Accordingly, a sand wheeled base 200 (which is an outside form of transport device) is needed that comprises a base frame 202 and oversized wheels 204 designed to easily roll in sandy terrain. In this case, the patient support deck 22 is placed on the sand wheeled base 200. More specifically, the sand wheeled base 200 has a support frame 206 defining a mounting cradle 208, much like the cradle 88 of the transport device 26 that receives the coupling device 52 of the patient support deck 22.

The patient support deck 22 may be selected by the emergency medical personnel at the scene based on the particular needs of the injured/ill person or based on their size, etc. Therefore, once the emergency medical personnel have initially assessed the scene, they can select an appropriate patient support deck 22 and/or appropriate wheeled base. Other types of wheeled bases that mate with all the different types of support decks 22 may be available for use, not only the sand wheeled base 200, but also smooth surface wheeled bases 300, like that shown in FIG. 13, or other bases particularly designed for helicopters, ambulances, or other terrain types, or bases designed for people with particular conditions, or bases with different levels of functionality, e.g., powered wheels, power actuated lifts, powered actuated deck sections, etc.

In FIG. 13, the smooth surface wheeled base 300 comprises a base frame 302 and normal sized wheels 304 designed to roll along smooth surfaces. In this case, the patient support deck 22 that was on the sand wheeled base 200 is lifted off the sand wheeled base 200 and placed on the smooth surface wheeled base 300, once the patient is cleared of the sandy terrain. The smooth surface wheeled base 300 is much easier to transport with its smaller, wheels 304 to the EMS vehicle. The smooth surface wheeled base 300 also comprises support frame 306 defining a mounting cradle 308, identical to the mounting cradle 208 of the sand wheeled base 200, so that the patient support deck 22 can be interchangeable mounted to and supported by the sand wheeled base 200 and the smooth surface wheeled base 300.

By virtue of providing different types of bases on which to support the patient, and by providing a patient support deck 22 designed to suit the particular patient, which is interchangeable with the different base types, the patient is able to stay on the same patient support surface during the entire mobilization effort by the EMS team outside of the healthcare facility. This includes keeping the patient on the same support surface from the time that the EMS team first places the patient on the patient support deck 22 through to the time that the patient support deck 22 is placed in the EMS vehicle, as shown in FIG. 13. In some embodiments, not shown, the patient support deck 22 may also be removed from the smooth surface wheeled base 300 prior to placement in the EMS vehicle with the patient support deck 22 being directly supported by the EMS vehicle floor, without underlying wheeled base. In this case, the EMS vehicle may also have a cradle (not shown) for receiving the coupling device 52 in a manner similar to the wheeled bases 200, 300. In other embodiments, the wheeled bases 200, 300 are also collapsible (notice scissor-lift frame configuration shown in FIG. 13) so that the bases can be collapsed for placement in the EMS vehicle. In cases where the EMS vehicle is a helicopter, the patient support deck 22 can be compatible with the helicopter by virtue of the coupling device 52 being releasably engageable with a cradle in the helicopter, so that there is no need for a separate base. In some cases, however, a separate helicopter-specific base may be employed. In further embodiments, the patient support decks 22 used with the EMS vehicle may be disposable, and/or could be stacked on other, sterilizable, patient support decks 22 at the healthcare facility, when the patient arrives, as described below.

Referring to FIGS. 14 and 15, in one embodiment, the goal of the patient support system 20 is to maintain the patient on the same patient support deck 22 not only outside of the healthcare facility, but in the healthcare facility, all the way from admission of the patient to discharge of the patient. As shown in FIG. 14, when the patient is first brought to the healthcare facility, the patient is first removed from the EMS vehicle, while still on the patient support deck 22. The same patient support deck 22 is then coupled to one of the transport devices 26 at the healthcare facility to bring the patient into the emergency room on the patient support deck 22. In some cases, the patient could be transferred to another type of patient support deck 22 at this point, or the patient support deck 22 could be stack on another patient support deck 22 being transported by the transport device 26. Once in the emergency room, the transport device 26 moves into proximity of one of the docking stations 24 in the emergency room and the docking station 24, by virtue of sensing the transport device 26 being within its proximity, autonomously engages the patient support deck 22 and removes it from the transport device 26 (step not shown). The docking station 24 could alternatively be controlled by a caregiver to move the manipulator 54 into position to remove the patient support deck 22 from the transport device 26. After the patient's condition has been assessed/treated, etc., the patient is then moved to a patient room, while staying on the same patient support deck 22. Accordingly, one of the transport devices 26 is called to the emergency room (e.g., via input device on the patient support deck 22 or docking station 24) and the manipulator 54 places the patient support deck 22 on the transport device 26 for delivery of the patient to their patient room. In the patient room, a different docking station 24 then detects the transport device 26 and/or the patient support deck 22 and engages the patient support deck 22 (step not shown).

Still referring to FIG. 14, in some cases, medical images of the patient may be needed during the patient's stay in the healthcare facility. When appropriate, a caregiver may call for a transport device 26 to come and pick up the patient support deck 22 with the patient supported thereon, for transport to the imaging room in the same manner as previously described. For instance, the docking station 24 may detect the presence of the transport device 26 without any patient support deck 22 and acknowledge that a request has been made for transport of the patient support deck 22. Accordingly, the manipulator 54 of the docking station 24 is autonomously operated once the transport device 26 is appropriately positioned to place the patient support deck 22 on the transport device 26 (or could be controlled by the caregiver). The patient support deck 22 and/or transport device 26 may comprise those specially designed for imaging, such as shown in FIGS. 5A-5C, which are specially designed for translating the patient support deck 22 toward and/or into an imaging device IMDEV as shown in FIG. 14 for taking an x-ray image, CT scan, or the like. Once the images are taken, the patient support deck 22 and/or transport device 26 return to their normal transport configurations (e.g., without the patient support deck 22 being extended) to prepare for transport back to the patient room, all without requiring any transfers of the patient to a different support surface.

Referring to FIG. 15, once the patient has been treated, or is otherwise ready for discharge (or transfer), a transfer device 26 is called to the patient room to carry the patient out of the healthcare facility, using the wheelchair functionality of the transport device 26. Once the patient is secured in the transport device 26 to be carried out of the patient room, the patient support deck 22 is ready for transport to the sterilization apparatus 28. In this case, a second transport device 26, possibly specially designed to carry patient support decks 22 to the sterilization apparatus 28, is called to the patient room to receive the used patient support deck 22. The used patient support deck 22 is then carried to the sterilization apparatus 28 and placed in the enclosure 100 for sterilization using the sterilization medium over a predetermined sterilization cycle. By sterilizing the patient support deck 22 at a location outside of the patient room, more room is available in the patient room, thereby reducing clutter in the patient room and improving turnaround times for readying a patient room for the next patient. Once sterilization is complete, the sterilized patient support deck 22 is stored in the storage facility 30 and ready for use by another patient. The storage facility 30 may be located adjacent the sterilization apparatus 28 for easy access and delivery of sterilized patient support decks 22 or may be more remotely located such that a transport device 26 is used to deliver the patient support decks to the storage facility 30.

Referring back to FIG. 2, the central controller 34 of the control system 32 can analyze information received from the patient support decks 22, the docking stations 24, the transport devices 26, the sterilization apparatuses 28, and the storage facilities 30 so that the central controller 34 knows the location, availability, and sterilization status of all of the patient support decks 22, and whether they are occupied or unoccupied. The central controller 34 is able to always account for the location, availability, status, etc., of all the patient support decks 22 by virtue of all the patient support decks 22 being associated with at least one of the docking stations 24, transport devices 26, sterilization apparatuses 28, and/or storage facilities 30 at all times. The central controller 34 is thereby able to determine whether the patient support decks 22 are available for use by patients and can display the availability of the patient support decks 22 on one or more of the displays D.

The central controller 34 may also be able to provide inventory management services by estimating the availability of the patient support decks 22, docking stations 24, transport devices 26, sterilization apparatuses 28, and/or storage facilities 30, such as by monitoring the current status of these components and accounting for time needed for the patient support decks 22, docking stations 24, transport devices 26, sterilization apparatuses 28, and/or storage facilities 30 to carry out current tasks, and the like. For instance, even though a patient support deck 22 may currently be in a sterilization apparatus 28 undergoing sterilization, the central controller 34 is able to determine the length of time until sterilization is complete and when the patient support deck 22 will be ready and can store/display that estimated time as the time that the patient support deck 22 will be available for a new patient. Similarly, if a patient support deck 22 is currently supporting a patient being discharged, the central controller 34 can estimate how long until the discharge will be complete, how long it will take a transport device 26 to carry the patient support deck 22 to the sterilization apparatus 28, and how long it will take to complete sterilization to make the patient support deck 22 ready for the next patient.

The central controller 34 can also determine the current usage of the patient support decks 22, the docking stations 24, the transport devices 26, the sterilization apparatuses 28, and/or the storage facilities 30, and can estimate when the patient support decks 22, the docking stations 24, the transport devices 26, the sterilization apparatuses 28, and/or the storage facilities 30 will be ready for use. Additionally, the central controller 34 can determine how many/which types of the patient support decks 22, the docking stations 24, the transport devices 26, the sterilization apparatuses 28, and/or the storage facilities 30 are being used, how many/which types of the patient support decks 22, the docking stations 24, the transport devices 26, the sterilization apparatuses 28, and/or the storage facilities 30 are available, and the usage history for each of the patient support decks 22, the docking stations 24, the transport devices 26, the sterilization apparatuses 28, and/or the storage facilities 30.

The central controller 34 is configured to generate an alert in response to a number of the patient support decks 22 in one or more of the storage facilities 30 reaching or falling below a predetermined threshold. For instance, if the number of patient support decks 22 available in one of the storage facilities 30 falls below ten, an audible, visual, or tactile alert can be sent to the docking stations 24, transport devices 26, sterilization apparatuses 28, and/or storage facilities 30 via the central controller 34. Similarly, the alerts can be customized for monitoring certain types of patient support decks 22. For instance, if the number of patient support decks 22 available in the storage facilities 30 for tall patients falls below two, an audible, visual, or tactile alert can be sent to the docking stations 24, transport devices 26, sterilization apparatuses 28, and/or storage facilities 30 via the central controller 34. The central controller 34 can also be configured to prevent storage in the storage facilities 30 of used and unsterilized patient support decks 22 by identifying the particular patient support deck 22 via its identification device ID, checking the current records stored in the control system 32 relating to that particular patient support deck 22 to check its last location, and noting that its last location was in a patient room or elsewhere, without any subsequent sterilization. The central controller 34 can also track how many times a particular patient support deck 22 has been sterilized.

The central controller 34 also knows what features are being operated on the patient support deck 22, such as whether a CPR release has been activated, and can send request signals to a transport device 26 to transport that particular patient support deck 22 to an intensive care unit or other location in response to the CPR release being activated. In this case, the back section 46 is movable between raised and lowered positions and the CPR release is configured to cause the back section 46 to move to the lowered position. A sensor, such as a contact switch, or other type of release indication device can be present on the patient support decks 22, the docking stations 24, or the transport devices 26 to send a corresponding release signal to the deck controller 36, docking controller 38, or transport controller 40, which then causes the controller receiving the signal to automatically generate a transport request signal in response to activation of the CPR release. Additionally, since the central controller 34 is able to assess the location of each of the transport devices 26 on the network NET, the central controller 34 is able to determine the location of the transport device 26 closest to the location at which the emergency has occurred to optimize response time during this emergency dispatch. It should also be noted that the central controller 34 is able to manipulate and process the data provided by the patient support decks 22, the docking stations 24, the transport devices 26, the sterilization apparatuses 28, the storage facilities 30, the ADT and the EMR in order to optimize the response time in several situations, including the response time to providing new patients with a suitable patient support deck 22, the response time for moving patients between locations for treatment, and the like.

The central controller 34 also knows if the docking stations 24 are occupied or unoccupied and what features are being operated on the docking stations 24. By virtue of these connections, the central controller 34 also knows important vital levels of patients, whether the patient has exited the patient support deck 22, if a patient has been newly admitted or discharged, and can send alerts to caregivers as needed, or send requests for a new patient support deck 22 from a storage facility 30, for a transport device 26 to carry a patient, and/or for a transport device 26 to move a patient support deck 22 from the sterilization apparatus 28, as needed.

The central controller 34 is also configured to keep records of transactions in the healthcare facility and to update records in other systems as applicable, such as records in an admission-discharge-transfer (ADT) system, electronic medical records (EMR) of the patient, or the like. The central controller 34 may be configured to transmit a transport request signal to one of the transport devices 26 to request delivery of one of the patient support decks 22 for a newly admitted patient in response to the ADT system generating a signal indicating admission of a new patient. The central controller 34, by knowing the location of all the transport devices 26 being used, can command the closest transport device 26 to the storage facility 30 storing the desired patient support deck 22 to retrieve the desired patient support deck 22. The central controller 34 is also configured to transmit a transport request signal to the transport device 26 to request retrieval of one of the patient support decks 22 associated with a discharged or transferred patient in response to the ADT system generating a signal indicating discharge or transfer of the patient. The central controller 34 can specifically request whether the transport device 26 is to be driven autonomously to deliver/retrieve the particular patient support deck 22 or whether a caregiver is to oversee the delivery/retrieval by manually transporting the patient support deck 22. In some cases, autonomous delivery/retrieval may not be permitted or feasible, or the particular location of the patient support deck 22 may be difficult to maneuver to without manual assistance by a caregiver.

The central controller 34 is able to maintain real time information on patients and patient locations throughout the healthcare facility, determine and store time that patients have been in current locations, identify and alert others to combative patients or patients that have certain critical conditions (e.g., patients requiring CPR), and track caregivers activities, such as when caregivers enter/exit rooms, activate features on the patient support decks 22, docking stations 24, and/or transport devices 26, based on identification devices ID, e.g., RFID tags or badges, worn by the caregivers or via information manually entered by the caregivers. The central controller 34 can also track all bed exits and associated alarms for a patient or when a particular alarm was activated and the response time of caregivers to such alarms. All of this information can also be transferred among any of the patient support decks 22, docking stations 24, transport devices 26, sterilization apparatuses 28, or storage facilities 30, and be used to track patient flow throughout the healthcare facility. Any of the information collected and/or analyzed by the central controller 34, can be displayed on the one or more displays D of the patient support decks 22, docking stations 24, transport devices 26, sterilization apparatuses 28, and storage facilities 30.

The central controller 34 may comprise one or more microprocessors for processing instructions or for processing an algorithm stored in memory to transmit, receive, and/or analyze information to/from the patient support decks 22, docking stations 24, transport devices 26, sterilization apparatuses 28, and/or storage facilities 30. In particular, the central controller 34 is in communication with the deck controllers 36, docking controllers 38, transport controllers 40, sterilization controllers 42, and/or storage controllers 44 to carry out these functions. The control system 32 may be configured so that any of the patient support decks 22, docking stations 24, transport devices 26, sterilization apparatuses 28, or storage facilities 30 can be controlled or interrogated from any location. For instance, transport request signals can be made from any location through the control system 32 to one of the transport devices 26.

For purposes of autonomous movement of the transport devices 26, the central controller 34 may be configured to update mapping of the healthcare facility based on internal mapping capabilities of the transport devices 26. For instance, the transport devices 26 may be manually operated for an initial period of time in order for the transport controllers 40, and by extension the central controller 34, to learn routes/paths in which the transport devices 26 can traverse to move between locations in the healthcare facility. After the initial period of time, all high traffic routes/paths will be known to the central controller 34 and stored in the memory M integral therewith for later retrieval by the transport devices 26 so that the transport devices 26 are able to move from one location to another by simply following the routes/paths previously stored. The routes/paths taken by the transport devices 26 can be determined by a local GPS system or other dynamic asset tracking system used to track movement of the transport devices 26 in the healthcare facility.

The controllers 34, 36, 38, 40, 42, 44 may comprise one or more computers, microcontrollers, field programmable gate arrays, systems on a chip, discrete circuitry, and/or other suitable hardware, software, or firmware that is capable of carrying out the functions described herein. The controllers 34, 36, 38, 40, 42, 44 may be carried on-board the patient support decks 22, docking stations 24, transport devices 26, sterilization apparatuses 28, and storage facilities 30, or may be remotely located. Power to the controllers 34, 36, 38, 40, 42, 44 may be provided by a battery power supply or an external power source.

The input devices I described herein may comprise any device capable of being actuated by the user, or sensors. The input devices I may be configured to be actuated in a variety of different ways, including but not limited to, mechanical actuation (hand, foot, finger, etc.), hands-free actuation (voice, foot, etc.), and the like. The input devices I may comprise buttons (such as buttons corresponding to lift, lower, back section raise/lower, foot section raise/lower, Trendelenburg, and reverse Trendelenburg), a gesture sensing device for monitoring motion of hands, feet, or other body parts of the user (such as through a camera), a microphone for receiving voice activation commands, a foot pedal, and a sensor (e.g., infrared sensor such as a light bar or light beam to sense a user's body part, ultrasonic sensor, etc.). Additionally, the buttons/pedals can be physical buttons/pedals or virtually implemented buttons/pedals such as through optical projection or on a touchscreen. The buttons/pedals may also be mechanically connected or drive-by-wire type buttons/pedals where a user applied force actuates a sensor, such as a switch or potentiometer. It should be appreciated that any combination of input devices I may also be utilized. The input devices I may be located at any suitable location. The input devices I may also be located on a portable electronic device (e.g., iWatch®, iPhone®, iPad®, or similar electronic devices).

Various electronic interfaces can be provided to caregivers, the patients, visitors, or others to take advantage of the interconnectivity of the system components of the patient support system 20, such as interfaces for reporting information from the patient support system 20, requesting services, or displaying such information. One such interface may be an application, such as a mobile application for an iOS operating system of a portable electronic device PED. This application may be configured to display on one screen different types of patient support decks 22 available and allow the user to simply drag & drop a graphical representation (or other type of representation) of a desired patient support deck 22 into a graphical representation (or other type of representation) of a desired location, which may be a patient room associated with the user, a patient room found in a look-up table in the application, a room typed into the application by the user, or a room automatically identified by the application based on location data, such as local GPS location data. This "drag & drop" action by the user causes the desired patient support deck 22 to be autonomously retrieved and transported to the desired location via one or more transport devices 26. Alternatively, this "drag & drop" action causes a request for such a transfer to be generated and fulfilled manually be one or more caregivers or other personnel in the healthcare facility.

The application may also enable a user to drag & drop a graphical or other representation of any patient support deck 22 into any location graphically or otherwise represented in the application, such as one of the sterilization apparatuses 28, one of the storage facilities 30, another location such as an imaging room or emergency room, or the like. The application may also enable users to receive alarms relating to the patient support decks 22 or associated patients, and their locations, such as bed exit alarms, CPR alarms, alarms regarding lifting and lowering of the patient support deck 22 via the docking station 24, patient temperature alarms, patient location alarms (e.g., via thermal imaging of the patient on the patient support decks 22), and the like. The application could also be used to set and deactivate such alarms and to configure other types of alarms. The application may also provide information such as current configurations of the patient support decks 22, current locations of patient support decks 22, sterilization status of patient support decks 22, and the like. As shown in FIG. 2, a portable electronic device PED operating such an application is shown connected to the network NET.

The network NET may be a local area network (LAN), a wide area network (WAN) such as the Internet, or any other suitable type of network for enabling communication between the system components. The central controller 34 may comprise one or more servers, databases, or other hardware or software necessary for carrying out the functions described herein. The system components can be connected to the network NET through various interfaces, including through the communication modules COMM, which may be transceivers, wireless routers, Ethernet connections, or other wired or wireless interfaces. Furthermore, several central controllers 34 may be provided at various locations in the healthcare facility. Also, each sterilization apparatus 28 and/or storage facility 30 may have their own sterilization controller 42 and storage controller 44, or a single controller may be used to control all of the sterilization apparatuses 28 or storage facilities 30.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support system comprising:
a patient support deck for supporting a patient, said patient support deck comprising a coupling device;
a transport device movable across a floor surface, said transport device configured to releasably engage said patient support deck to carry said patient support deck across the floor surface, and said transport device comprising a transport controller and a communication module coupled to said transport controller;
a docking station comprising a manipulator having a mounting device configured to releasably engage said coupling device of said patient support deck and remove said patient support deck from said transport device when said patient support deck is carried by said transport device into a proximity of said manipulator, and said manipulator comprising:
a base movable in at least one degree of freedom relative to the floor surface,
an arm movable in at least one degree of freedom relative to said base, wherein said base carries said arm and is rotatable with said arm relative to the floor surface, a first actuator coupled to said base for rotating said base, and a second actuator coupled to said arm for pivoting said arm relative to said base;

a docking controller and an input device in communication with said docking controller, said input device configured to generate an input signal to cause said manipulator to move said arm autonomously to engage said patient support deck; and a storage facility sized to house said patient support deck;

wherein said manipulator and said patient support deck are configured so that said patient support deck is movable in at least three degrees of freedom relative to the floor surface after removal of said patient support deck from said transport device;

wherein at least one of said patient support deck and said docking station comprises a transport request device configured to generate a transport request signal to call said transport device via said communication module; and wherein said transport device comprises an autonomous driving system operable to autonomously drive said transport device to said proximity of said docking station in response to said transport request signal, said transport device being operable to autonomously drive into proximity of said storage facility to retrieve said patient support deck from said storage facility.

2. The patient support system of claim 1, wherein said manipulator and said patient support deck are configured so that said patient support deck is capable of being lifted, lowered, tilted, and rotated after removal of said patient support deck from said transport device.

3. The patient support system of claim 1, wherein said input device is mounted to said transport device such that said input signal is generated automatically by said input device in response to said transport device being in said proximity of said docking station.

4. The patient support system of claim 1, wherein said arm extends from said base to a distal end and said manipulator comprises said mounting device at said distal end for engaging said coupling device of said patient support deck.

5. The patient support system of claim 4, wherein said coupling device comprises a first interface for being releasably engaged by said transport device and a second interface for being releasably engaged by said mounting device.

6. The patient support system of claim 5, wherein said interfaces comprise ports configured to automatically connect to at least one of a data service, a communication service, a power service, a medical gas service, a vacuum service, a hydraulic service, or a pressurized air service from said transport device, said docking station, or a storage facility upon engagement of said patient support deck by said transport device, said docking station, or said storage facility.

7. The patient support system of claim 6, wherein said mounting device is shaped to mate with said second interface.

8. The patient support system of claim 5, wherein said mounting device comprises opposed mounting surfaces and said second interface comprises opposed interface surfaces congruent in orientation with said opposed mounting surfaces.

9. The patient support system of claim 5, wherein said patient support deck comprises a back section, a foot section, and a seat section, said back section and said foot section being movable relative to said seat section.

10. The patient support system of claim 9, wherein said first interface is fixed to said seat section and said second interface is fixed to said seat section.

11. The patient support system of claim 1, comprising a second patient support deck wherein said transport device and said docking station are configured to releasably engage said second patient support deck, said patient support decks having different configurations, wherein said different configurations comprise at least one of different widths, different lengths, different shapes, different weights, and different accessories.

12. The patient support system of claim 1, wherein said transport device is configured to provide at least one of a data service, a communication service, a power service, a medical gas service, a vacuum service, a hydraulic service, or a pressurized air service to said patient support deck upon engagement of said patient support deck by said transport device.

13. The patient support system of claim 1, wherein said docking station is configured to provide at least one of a data service, a communication service, a power service, a medical gas service, a vacuum service, a hydraulic service, or a pressurized air service to said patient support deck upon engagement of said patient support deck by said docking station.

14. The patient support system of claim 1, wherein said patient support deck comprises a battery and at least one of said transport device and said docking station comprises an inductive charging device configured to inductively charge said battery when said patient support deck is engaged by said at least one of said transport device and said docking station.

15. The patient support system of claim 1, wherein said patient support deck comprises a back section movable between raised and lowered positions and a CPR release configured to cause said back section to move to said lowered position, wherein said transport request device generates said transport request signal in response to activation of said CPR release.

16. The patient support system of claim 1, wherein said manipulator is configured to autonomously move said patient support deck into engagement with said transport device in response to said transport device being moved into said proximity of said docking station.

17. The patient support system of claim 1, wherein said docking station is configured to be ceiling-mounted.

18. The patient support system of claim 1, comprising a second docking station comprising a second manipulator configured to releasably engage and remove said patient support deck from said transport device when said patient support deck is carried by said transport device into a second proximity of said second manipulator, wherein said docking stations have different configurations.

19. The patient support system of claim 1, wherein said transport device comprises a seat portion and a back portion and is configured to operate as a wheelchair when disengaged from said patient support deck.

20. The patient support system of claim 1, wherein said patient support deck is free of power sources, electronics, movable side rails, lift systems, and wheels.

21. A patient support system comprising:

a patient support deck for supporting a patient, said patient support deck comprising a coupling device;

a transport device movable across a floor surface, said transport device configured to releasably engage said patient support deck to carry said patient support deck across the floor surface, and said transport device comprising a transport controller and a communication module coupled to said transport controller;

a docking station comprising a manipulator having a mounting device configured to releasably engage said coupling device of said patient support deck and remove said patient support deck from said transport device when said patient support deck is carried by said transport device into a proximity of said manipulator; and a storage facility sized to house said patient support deck;

wherein said manipulator and said patient support deck are configured so that said patient support deck is movable in at least three degrees of freedom relative to the floor surface after removal of said patient support deck from said transport device;

wherein at least one of said patient support deck and said docking station comprises a transport request device configured to generate a transport request signal to call said transport device via said communication module; and wherein said transport device comprises an autonomous driving system operable to autonomously drive said transport device to said proximity of said docking station in response to said transport request signal, said transport device being operable to autonomously drive into proximity of said storage facility to retrieve said patient support deck from said storage facility.

22. The patient support system of claim 21, wherein said manipulator comprises:

a base movable in at least one degree of freedom relative to the floor surface;

an arm movable in at least one degree of freedom relative to said base, wherein said base carries said arm and is rotatable with said arm relative to the floor surface;

a first actuator coupled to said base for rotating said base; and a second actuator coupled to said arm for pivoting said arm relative to said base.

23. The patient support system of claim 22, wherein said arm extends from said base to a distal end and said manipulator comprises said mounting device at said distal end for engaging said coupling device of said patient support deck.

24. The patient support system of claim 23, wherein said coupling device comprises a first interface for being releasably engaged by said transport device and a second interface for being releasably engaged by said mounting device.

25. The patient support system of claim 24, wherein said patient support deck comprises a back section, a foot section, and a seat section, said back section and said foot section being movable relative to said seat section.

26. The patient support system of claim 21, wherein said transport device comprises a seat portion and a back portion and is configured to operate as a wheelchair when disengaged from said patient support deck.

* * * * *